United States Patent [19]
DiFoggio et al.

[11] Patent Number: 5,360,972
[45] Date of Patent: Nov. 1, 1994

[54] METHOD FOR IMPROVING CHEMOMETRIC ESTIMATIONS OF PROPERTIES OF MATERIALS

[75] Inventors: Rocco DiFoggio, Houston; Maya Sadhukhan, Katy; Martha L. Ranc, Houston, all of Tex.

[73] Assignee: Western Atlas International, Inc., Houston, Tex.

[21] Appl. No.: 107,953

[22] Filed: Aug. 17, 1993

[51] Int. Cl.⁵ .............................................. G01J 3/42
[52] U.S. Cl. .......................... 250/339.12; 250/339.09; 250/343; 364/498
[58] Field of Search .............. 250/343, 339.12, 339.09; 364/497, 498

[56] References Cited

U.S. PATENT DOCUMENTS

4,963,745 10/1990 Maggard ............................. 250/343
5,139,334 8/1992 Clarke .................................. 356/301

OTHER PUBLICATIONS

Analytical Chemistry, vol. 61 No. 4, Feb. 15, 1989, "Prediction of Gasoline Octane Numbers from New-Infrared Spectral Features in the Range 660–1219 nm", Kelly et al.

Primary Examiner—Paul M. Dzierzynski
Assistant Examiner—David Vernon Bruce
Attorney, Agent, or Firm—Elizabeth W. Layman

[57] ABSTRACT

The present invention is a method for improving the estimation of physical properties of a material, based on the infrared spectrum of the material, by concatenating additional data obtained from other measurement techniques to the infrared spectrum to fill the voids in the spectral data resulting from a lack of sensitivity by infrared spectrometers to trace compounds in the material. The augmented spectral data then is used to produce a calibration model for estimating the physical properties of the material.

14 Claims, 15 Drawing Sheets

METHOD FOR IMPROVING CHEMOMETRIC ESTIMATIONS OF PROPERTIES OF MATERIALS

FIELD OF THE INVENTION

This invention relates generally to a method for improving the correlative (chemometric) estimations of properties of materials from their infrared spectra by incorporating supplemental data from other measurement techniques. A particular example is a method to improve the estimations of octane numbers of gasolines that are based on correlations to the gasolines' infrared spectra by incorporating additional information provided by gas chromatography, Raman spectroscopy, or by lead, sulfur, or manganese analyzers along with the infrared spectra to compensate for the voids in the infrared data.

BACKGROUND OF THE INVENTION

Materials with different compositions exhibit slight, but measurable, differences in their absorption of near-infrared radiation. Thus, near-infrared analysis can be used to estimate the chemical composition and corresponding physical properties of materials as described in the patent application "METHOD FOR IMPROVING INFRARED ANALYSIS ESTIMATIONS BY AUTOMATICALLY COMPENSATING FOR INSTRUMENT INSTABILITIES" by DiFoggio, et al (U.S. Ser. No. 07/917,486) incorporated herein by reference.

Near-infrared (NIR) analysis is a secondary (indirect) analytical technique that is calibrated against primary (direct) analytical techniques (primary reference methods). NIR analysis requires a calibration or training set of samples of the material for which both the near-infrared spectra and primary reference measurements of the properties of interest are obtained.

Using regression mathematics, the NIR spectra of the calibration set is correlated to the primary reference measurements of the properties of these samples. The resulting regression models allow the estimation of the properties of unknown samples of material (ones for which primary reference measurements have not been made) from their NIR spectra.

NIR analysis has been applied in the petrochemical industry for analysis of both chemical composition (aromatic and saturates content) and physical properties (octane number, density, vapor pressure) of hydrocarbons including gasoline.

Octane-number ratings are a measure of the resistance of a gasoline to engine knock. There are two basic types of octane-number ratings corresponding to the conditions under which the engine test is performed. For the same gasoline, the less severe test (Research Octane Number or RON) produces higher octane-number ratings than does the more severe test (Motor Octane Number or MON). The average of RON and MON is called road octane number or (RON+MON)/2 because it represents an average performance of a gasoline under conditions of varying severity as would occur when actually driving on a road. This average also is called Pump Octane Number (PON) because it is the number which is usually posted at gas station pumps.

Generally, it is easier to use NIR to estimate chemical composition than to estimate physical properties of samples because NIR mainly measures the absorbance of vibrational modes whose number and types are determined by the chemical composition. NiR is able to estimate physical properties because the physical properties are related to the chemical composition in complex, and generally unknown, ways.

The regression models obtained from NIR analysis often lack generality. A calibration model which works well on a calibration set of samples may not work as well on unknowns. Additionally, it may not be possible to obtain a universal model that provides a satisfactory fit for all samples in calibration sets that consist of very diverse samples. Results of recent experimentation indicate that one reason for not being able to obtain a universal model is due to a fallacy in the underlying assumptions of the NIR technique itself.

One fundamental assumption of near-infrared and mid-infrared analysis is that all information needed to estimate a property of interest for a sample is contained within the infrared spectrum of that sample. If this assumption was correct, the development of a correlation model would be a straight-forward mathematical exercise of finding the most appropriate model or series of models for extracting the information contained in the spectrum.

Current work and published literature in this field are based on this fundamental assumption being valid for infrared analysis of unleaded gasolines. Failures in a model's ability to estimate unknown samples are ascribed to such things as using too small a calibration set, using a non-representative calibration set, the need to use more mathematics in manipulating the data, or incorrect values reported by the primary reference method. Poor estimations of octane number have not been attributed by the prior art to an absence of essential information in the infrared spectrum itself.

To test the fundamental NIR assumption, the spectra of 13,700 gasoline samples collected on-line at a refinery were used to develop a calibration model for octane number. Even with a calibration set of this magnitude, however, the model did not hold up over time.

Gas chromatography, infrared (IR), Raman and other analysis then were performed on gasoline samples for which NIR data also was available. The research indicated that the fundamental assumption noted above was flawed and that near and mid-infrared spectra have some information voids or "blind spots". For example, compounds that exist in trace amounts in a gasoline often have so small an effect on the spectrum that the effect is lost in the instrument noise and the interferences from a myriad of other compounds.

The use of gas chromatography (GC) as a stand-alone technique to estimate octane numbers has been described in the art for over twenty years. The prior art indicates that it takes a long time to generate a gas chromatogram and that even if all the components in a gasoline are known, the gasoline's octane number cannot accurately be determined by simple linear modeling because the octane number is not quite equal to the volume fraction of each component multiplied by its octane blending value because of interaction terms (the degree to which one component influences the effective octane number of another component) and other non-linear effects.

Hirschfeld suggested the use of NIR as a stand-alone technique to estimate octane number in 1984 in an article titled "Near-Infrared Reflectance Spectrometry: Tip of the Iceberg" (*Analytical Chemistry*, Vol 56, No. 8, July 1984, pp 933A–934A) that discussed applications of the 1100–2500 nm region of the near-infrared spectrum.

In early 1989, Kelly, et al of the Center for Process Analytical Chemistry (CPAC) at the University of Washington reported in "Prediction of Octane Numbers from Near-Infrared Spectral Features in the Range 660–1215 nm" (*Analytical Chemistry*, Vol. 61, No. 4, Feb. 15, 1989, pp 313–320) that octane numbers could be correlated to near-informed spectral features in the 3rd-overtone region (850–1050 nm). Kelly used a set of 43 unleaded California summer gasolines.

In late 1989, Maggard applied for a patent on using the 2nd-overtone region (1100–1250 nm) of the near-infrared for octane-number estimation (U.S. Pat. No. 4,963,745). Using his own training set of 90 gasoline samples (whose origin and degree of diversity are not specified), Maggard compared his own correlation to PON (R=0.9941 and SEC=0.497) using the three 3rd-overtone wavelengths (896, 932 and 1032 nm suggested in the Kelly paper) to his own correlation to PON (R=0.9887 and SEC=0.414) that was based on a single 2nd-overtone (1220 nm) wavelength. Although Maggard concluded that his invention, with only its single wavelength, provided better accuracy than Kelly's multiple correlation, it is shown below that Maggard's conclusions are not universally applicable but rather depend on the specific training set used.

It is widely known and accepted that trace amounts (on the order of 1%) of compounds cannot be accurately quantified using near-infrared spectroscopy. These trace amounts of compounds, however, can have a substantial effect on the octane number despite having little effect on the infrared spectra. For example, gasoline components such as normal decane (pure component RON rating of $-57$, and typical RON blending value of $-33$ octane numbers) can have a high impact on the octane number even when present in trace amounts: 1% of decane reduces the research octane number of a typical gasoline by 0.33.

Although it is generally accepted that NIR cannot accurately predict the octane number of leaded gasoline because the small amounts of tetraethyl lead that are used have a large impact on the octane number without significantly changing the NIR spectrum, the dramatic impact on an estimated octane number caused by the NIR missing other important trace compounds, such as the pure hydrocarbons nonane and decane, has been overlooked or ignored by the prior art. The effects of these missed trace compounds are the problem addressed by the present invention.

SUMMARY OF THE INVENTION

Errors in infrared estimations of properties resulting from the inability of infrared to accurately quantify some trace compounds are reduced by the present invention. The method incorporates applicable data determined from other measurements (such as gas chromatograms, Raman spectra, IR spectra and possibly other analyzer data for sulfur, lead and manganese percentages) with the NIR spectral data to develop better, more complete, more general and more reliable models for estimation of the octane number of motor fuels.

BRIEF DESCRIPTION OF THE TABLES AND DRAWING FIGURES

Table 1 is a listing of the octane ratings of a 26-sample NEG Calibration Set and percentages of some high-impact trace components contained in the samples.

Table 2a illustrates the results of 5-parameter regressions on the NEG Calibration Set of Table 1 using NIR, IR, GC, and Raman data, individually, and in all possible double and triple combinations.

Table 2b shows the results of the NEG Calibration Set of Table 1 using the projections (scores) of NIR, IR, GC, and Raman data along their corresponding principal components, individually, and in combination with the original NIR, IR, GC and Raman data.

Table 3 shows the intercorrelations between absorbance data at some wavelengths that are highly correlated to PON for a 277-sample Calibration Set of U.S. gasolines.

FIGS. 1a–d illustrate sample NIR, IR, Raman spectra and gas chromatogram, respectively, of a regular-octane gasoline (sample#1 of Table 1 whose PON=87.25).

FIGS. 2a–d illustrate sample NIR, IR, Raman spectra and gas chromatogram, respectively, of an intermediate-octane gasoline (sample#13 of Table 1 whose PON=89.25).

FIGS. 3a–d illustrate sample NIR, IR, Raman spectra and gas chromatogram, respectively, of a high-octane gasoline (sample#15 of Table 1 whose PON=93.10).

DETAILED DESCRIPTION

Figure 1A:
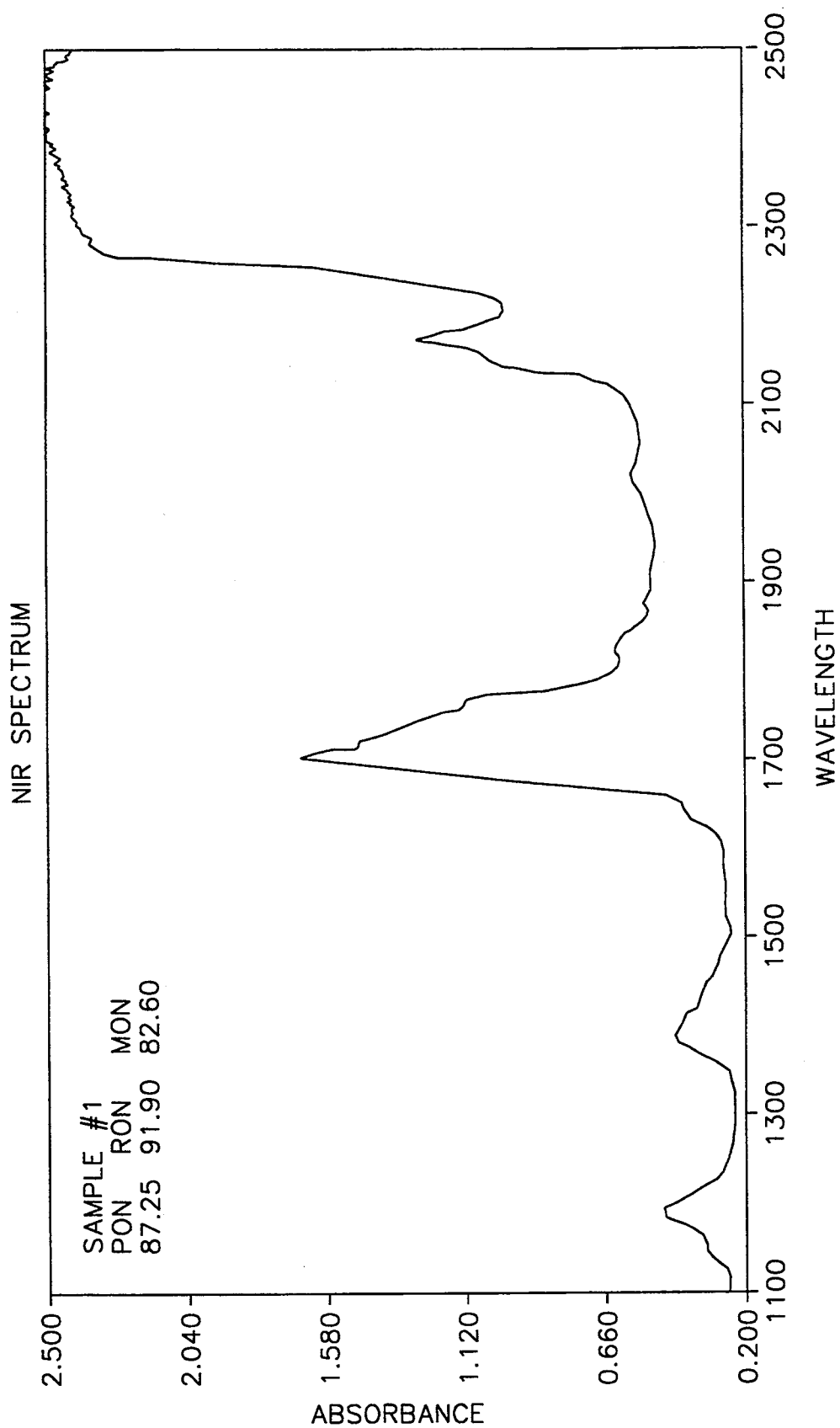
Figure 1B:
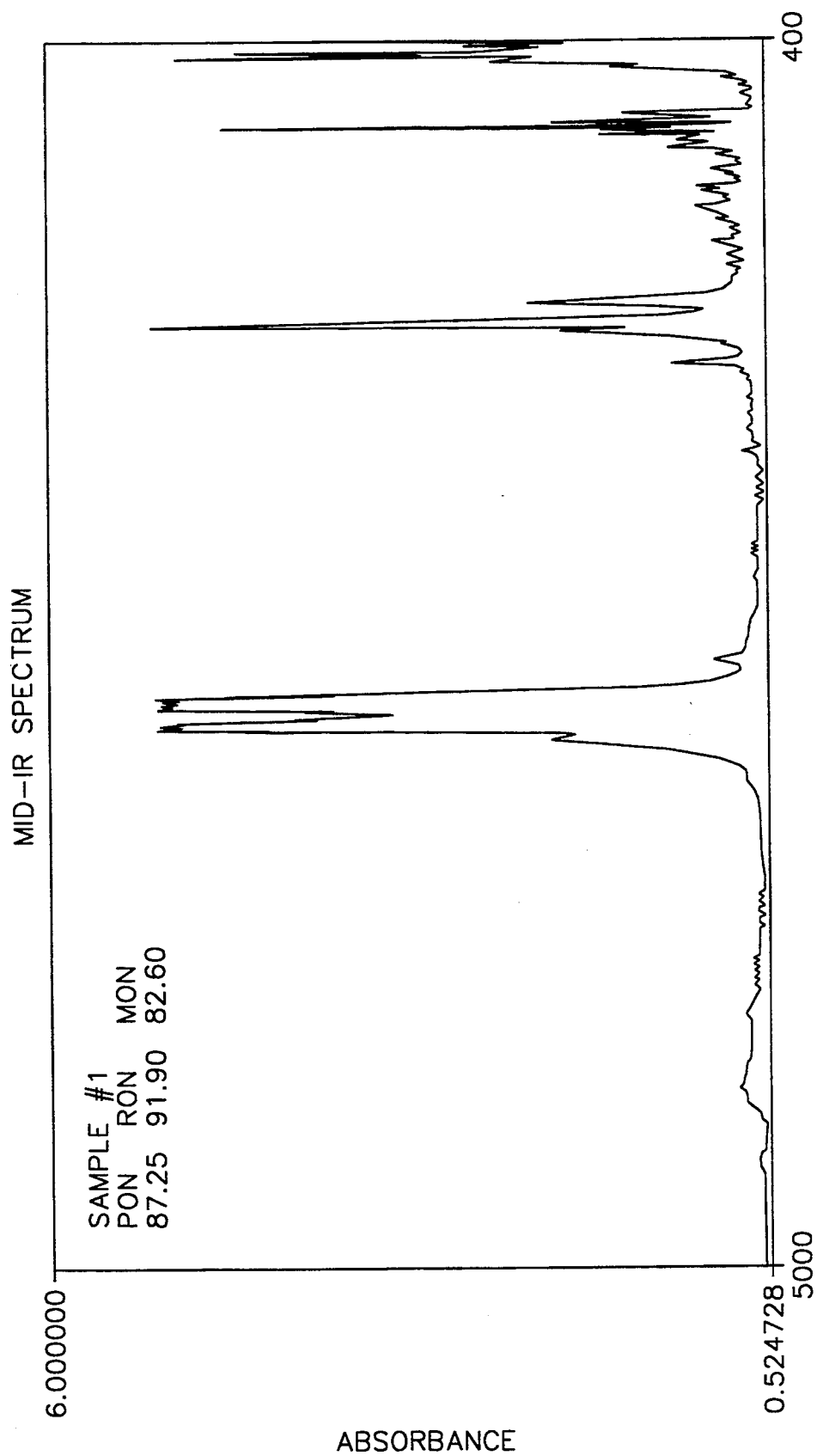
Figure 1C:
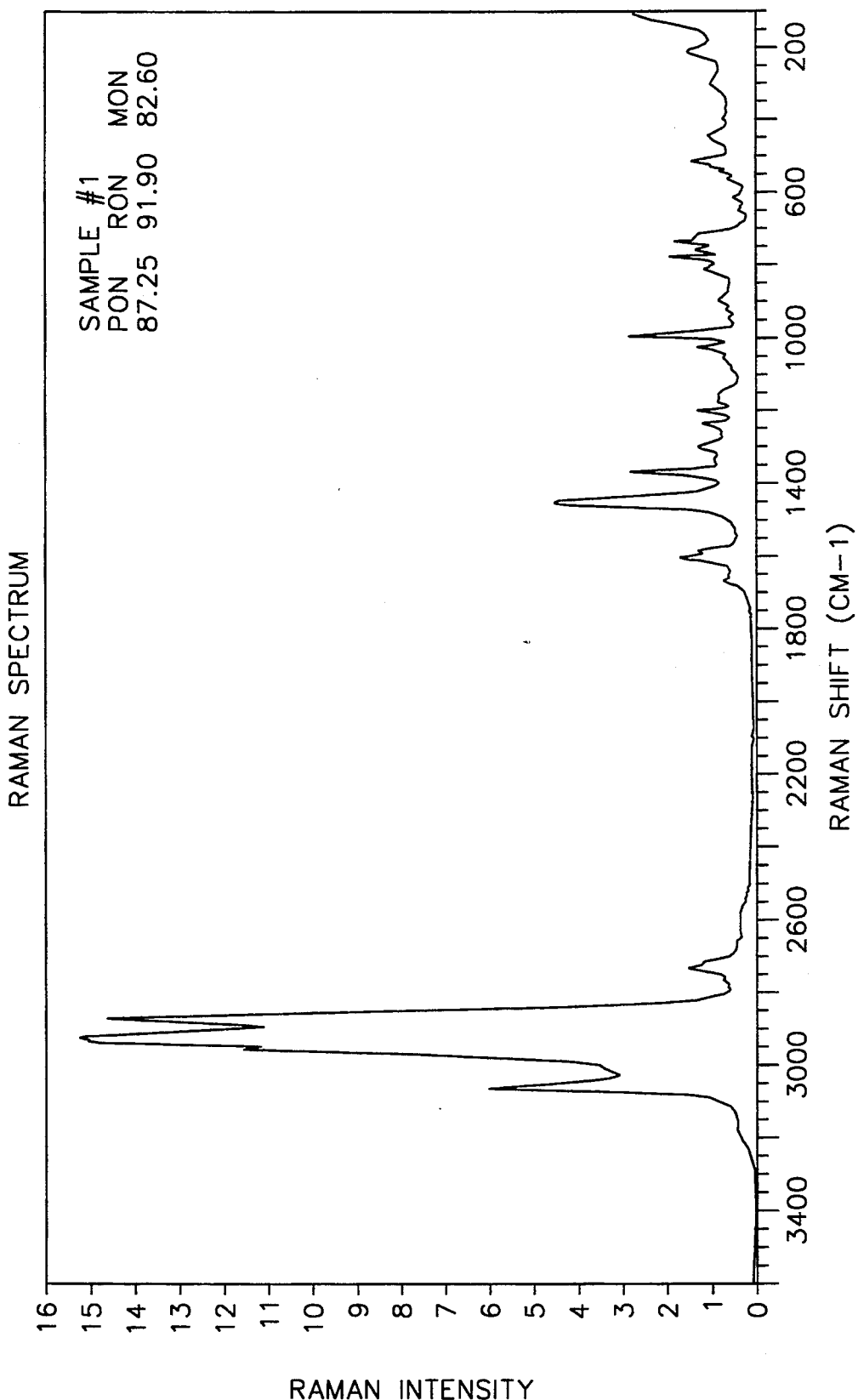
Figure 1D:
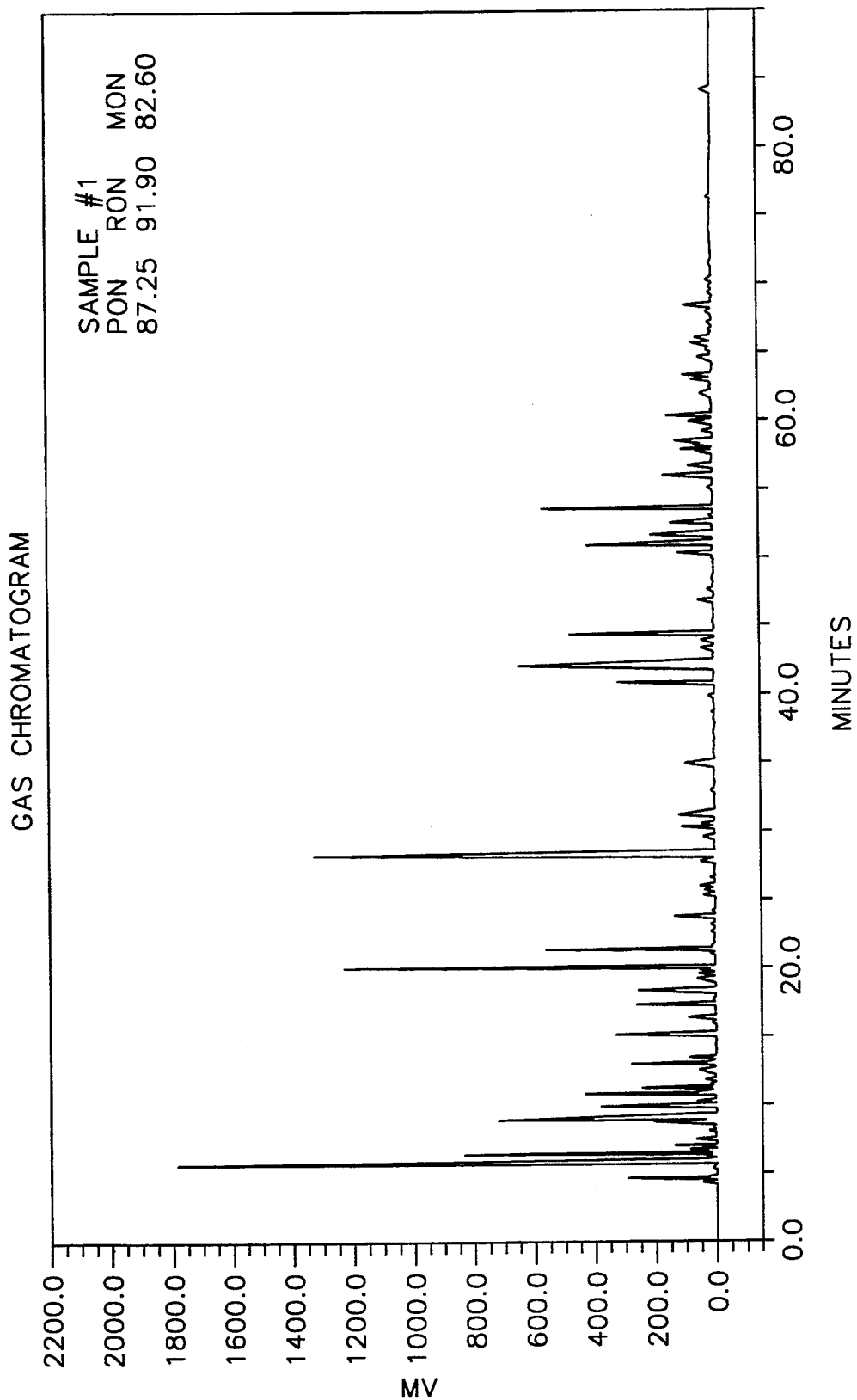
Figure 2A:
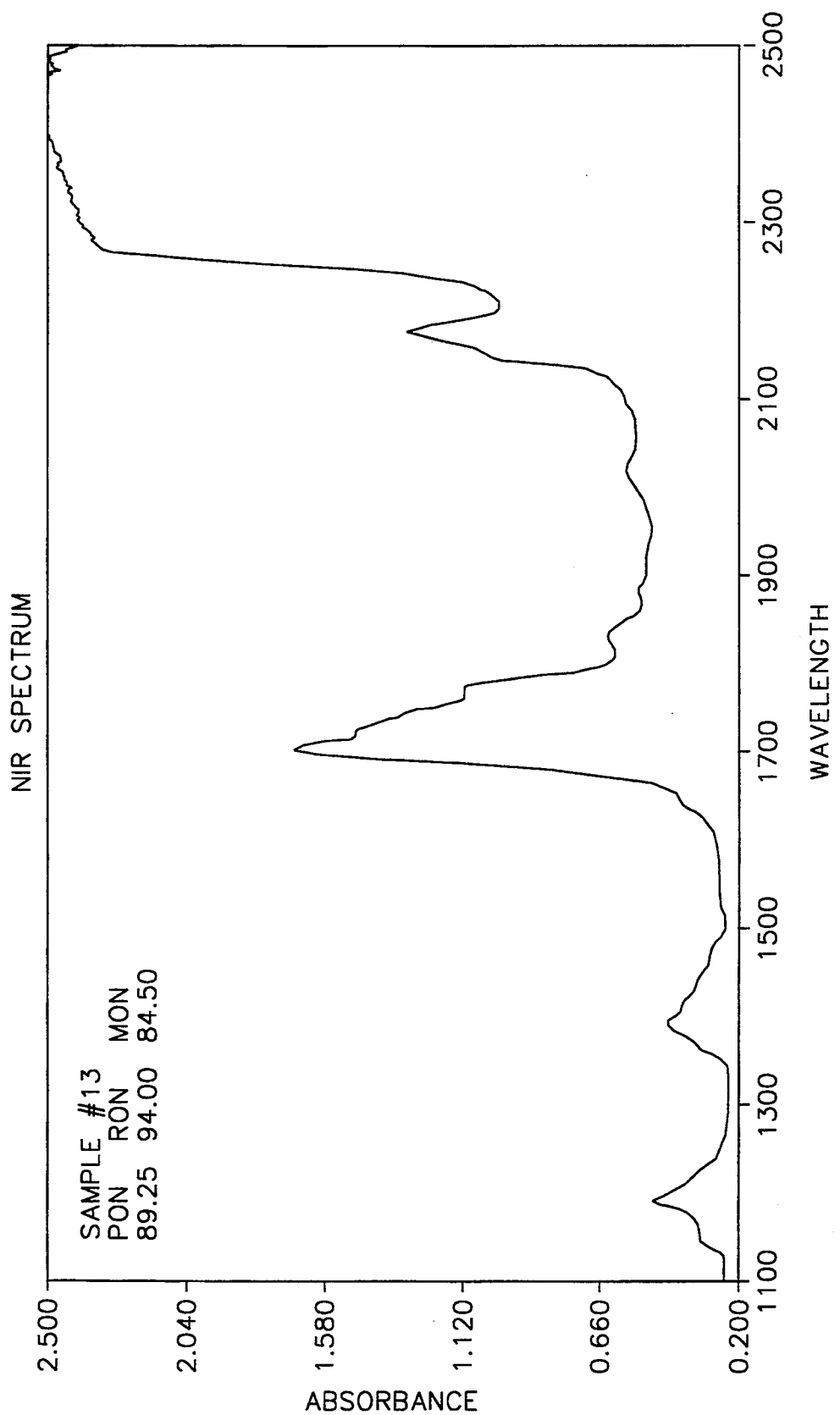
Figure 2B:
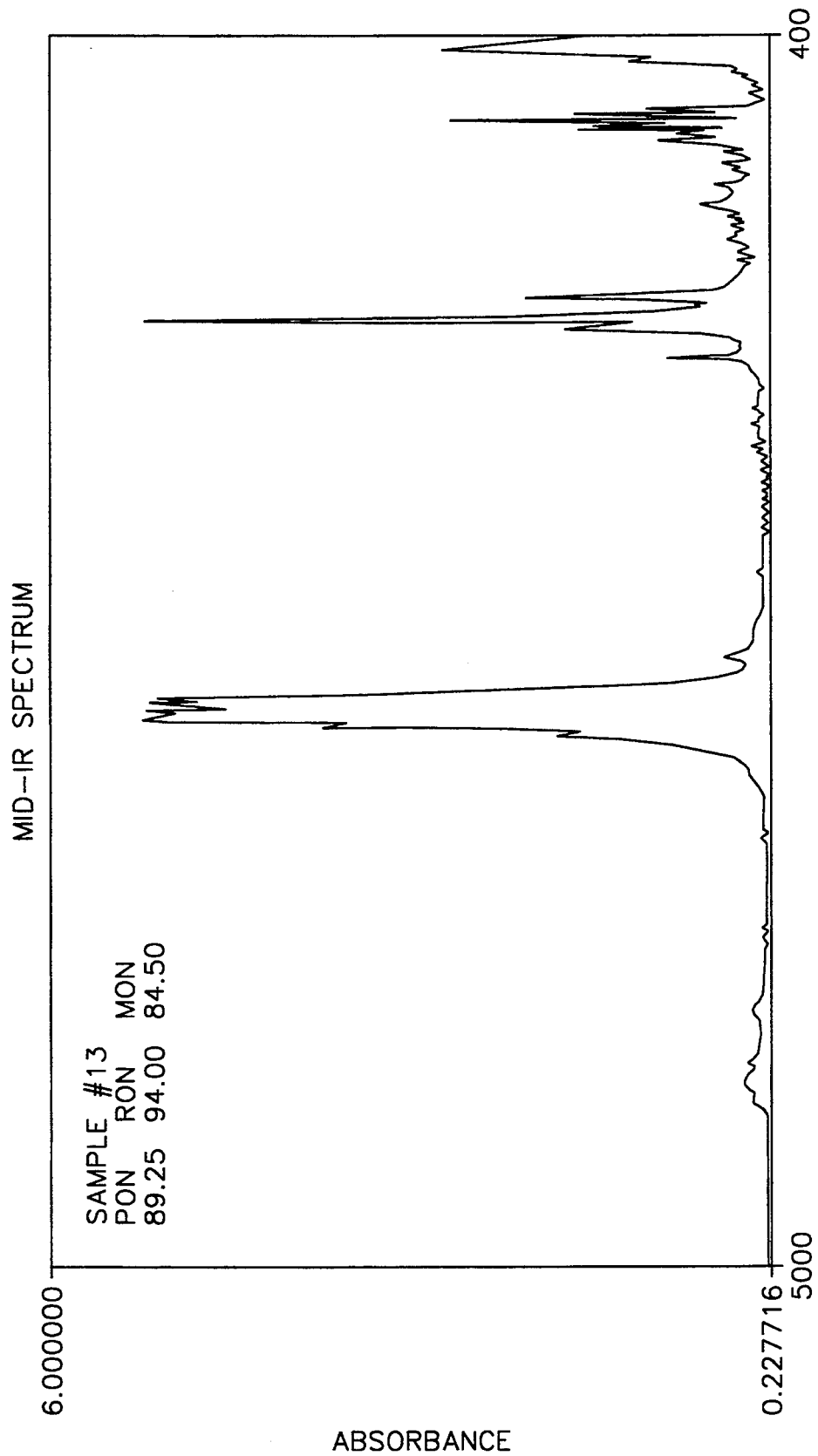
Figure 2C:
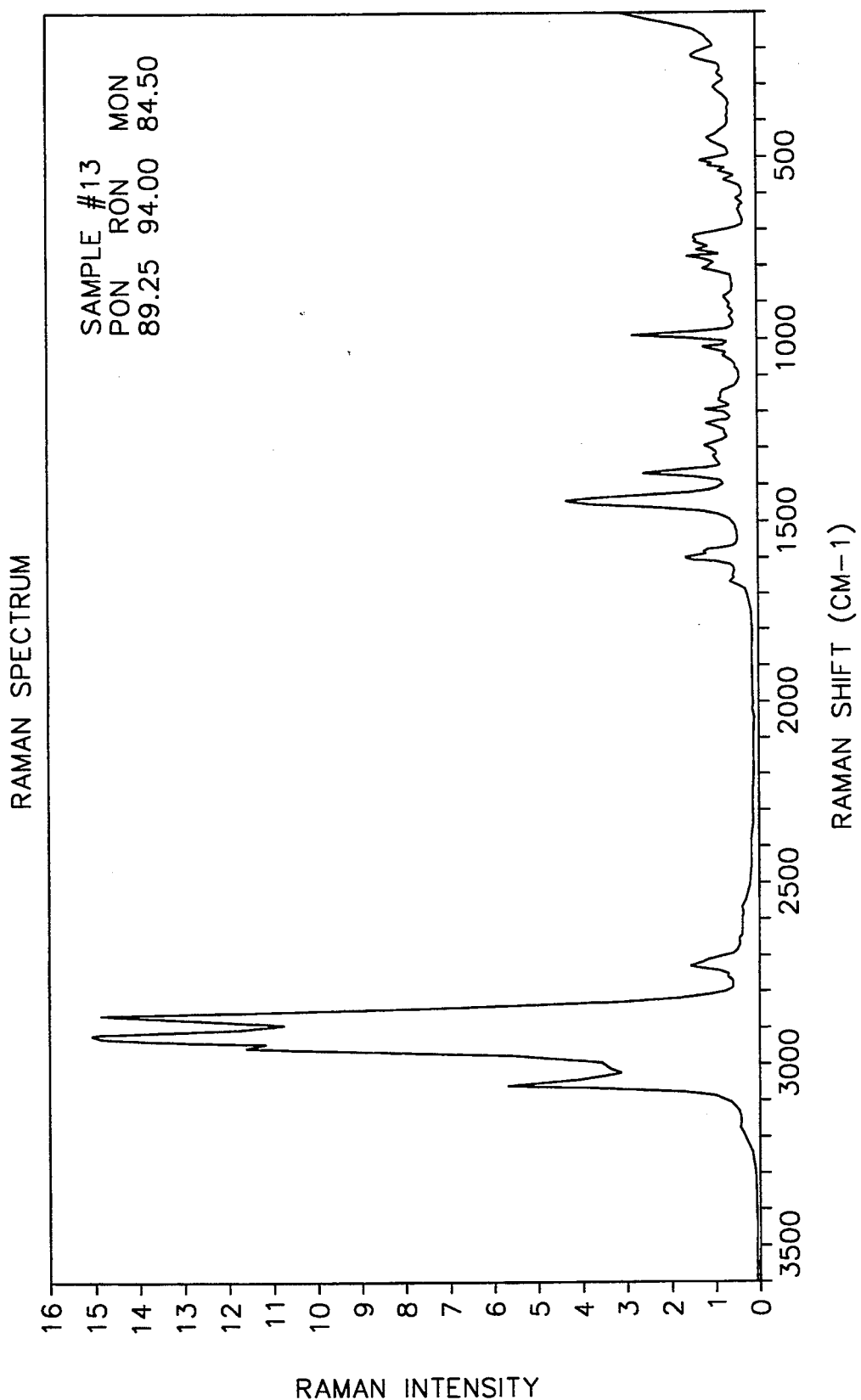
Figure 2D:
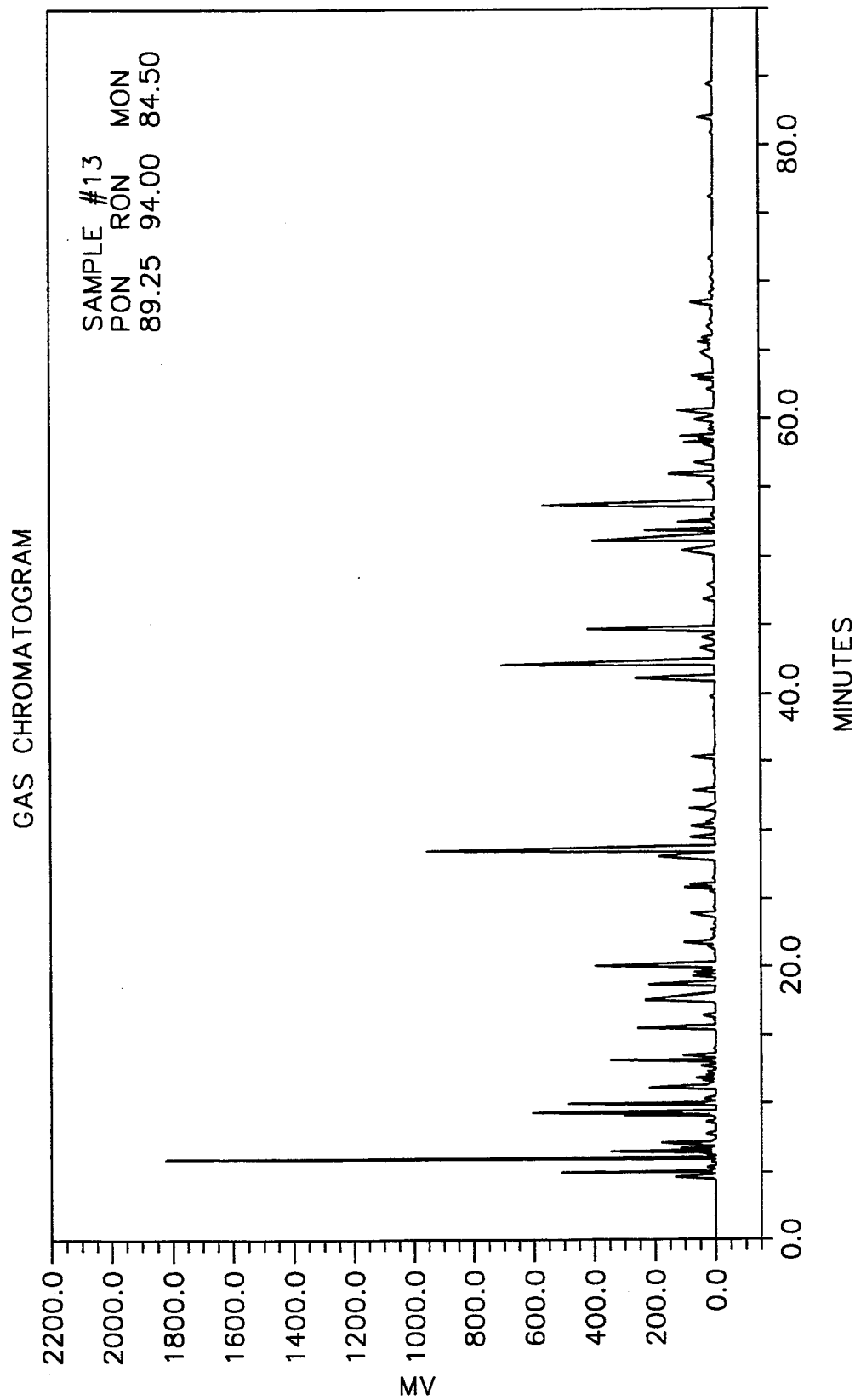
Figure 3A:
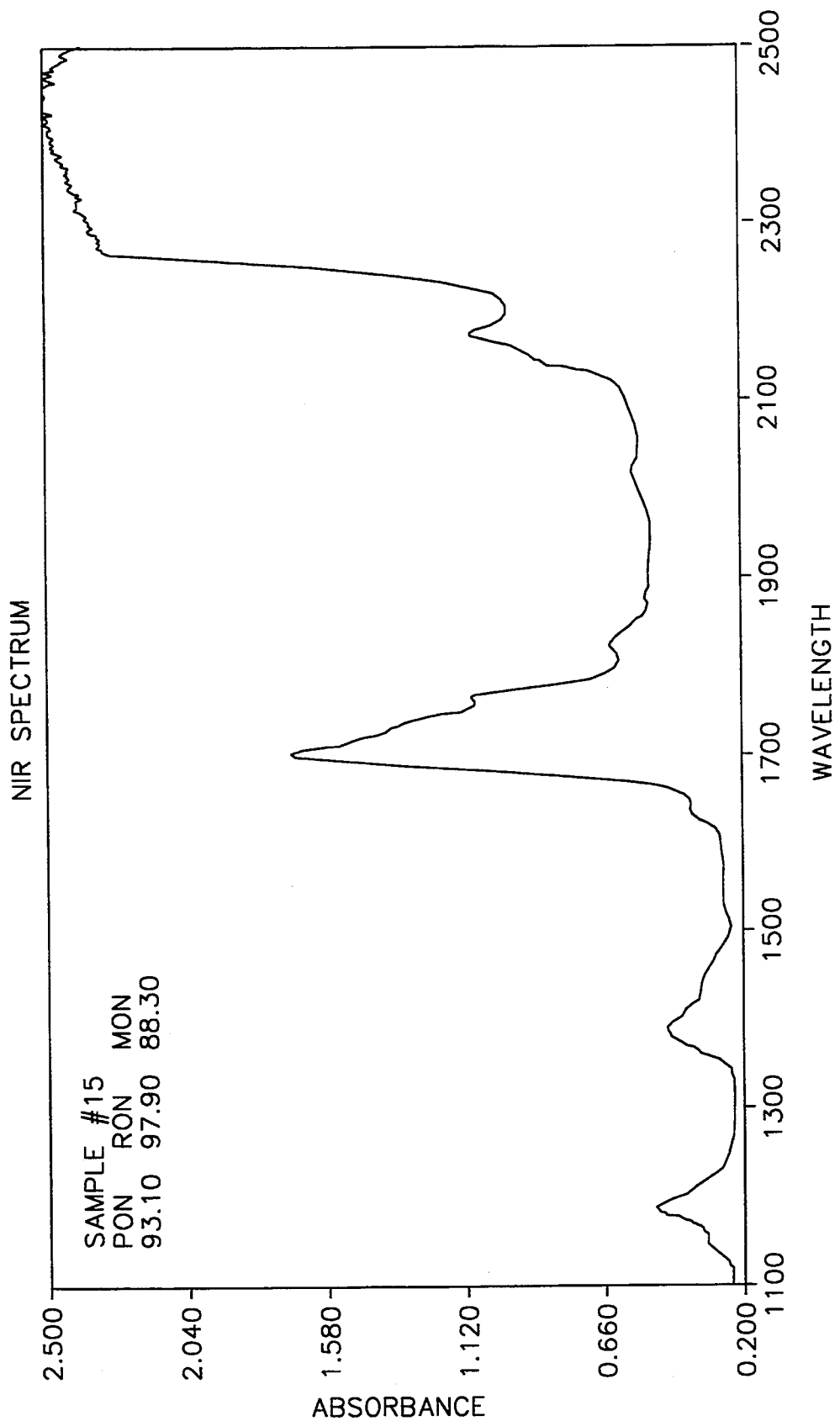
Figure 3B:
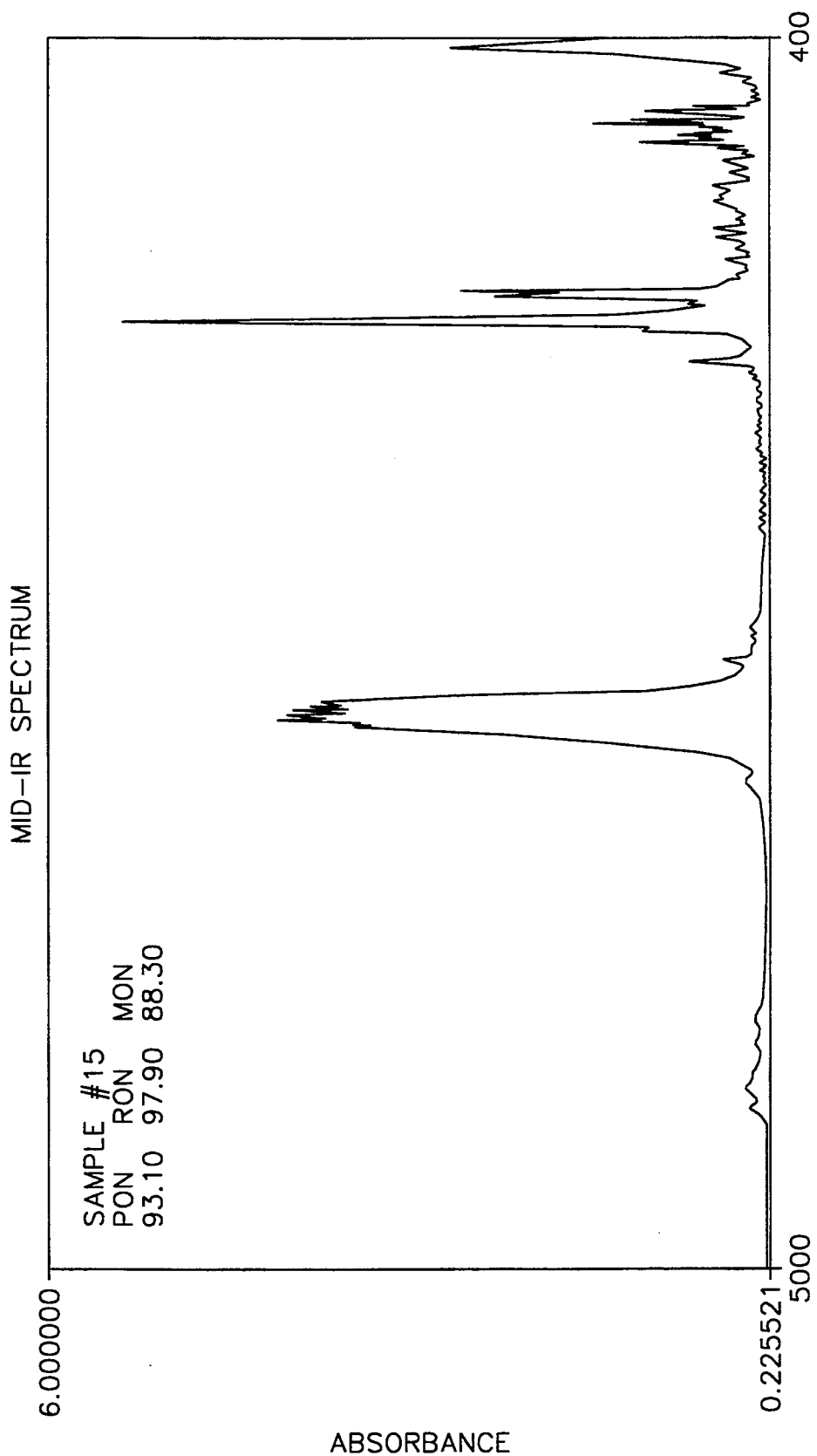
Figure 3C:
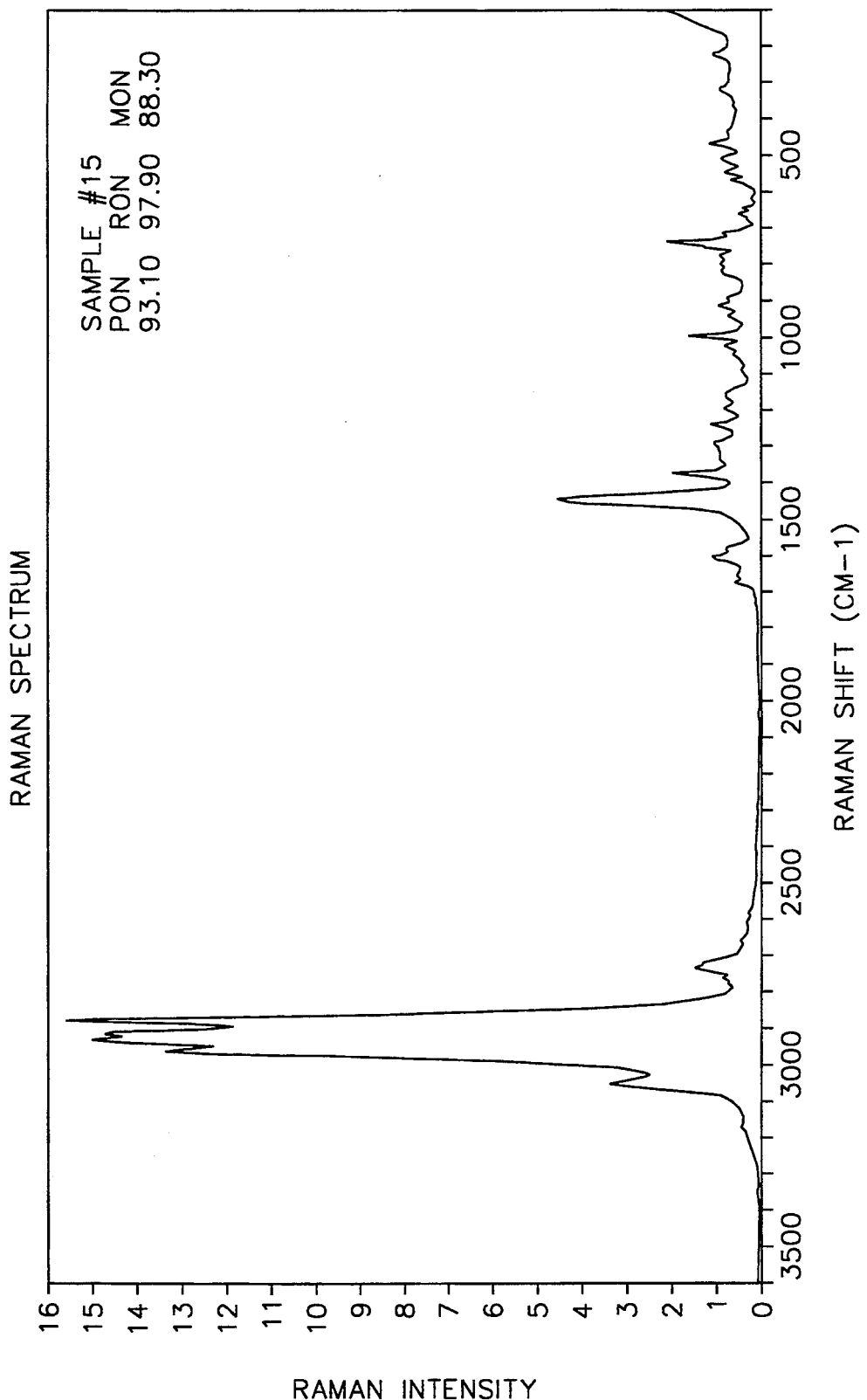
Figure 3D:
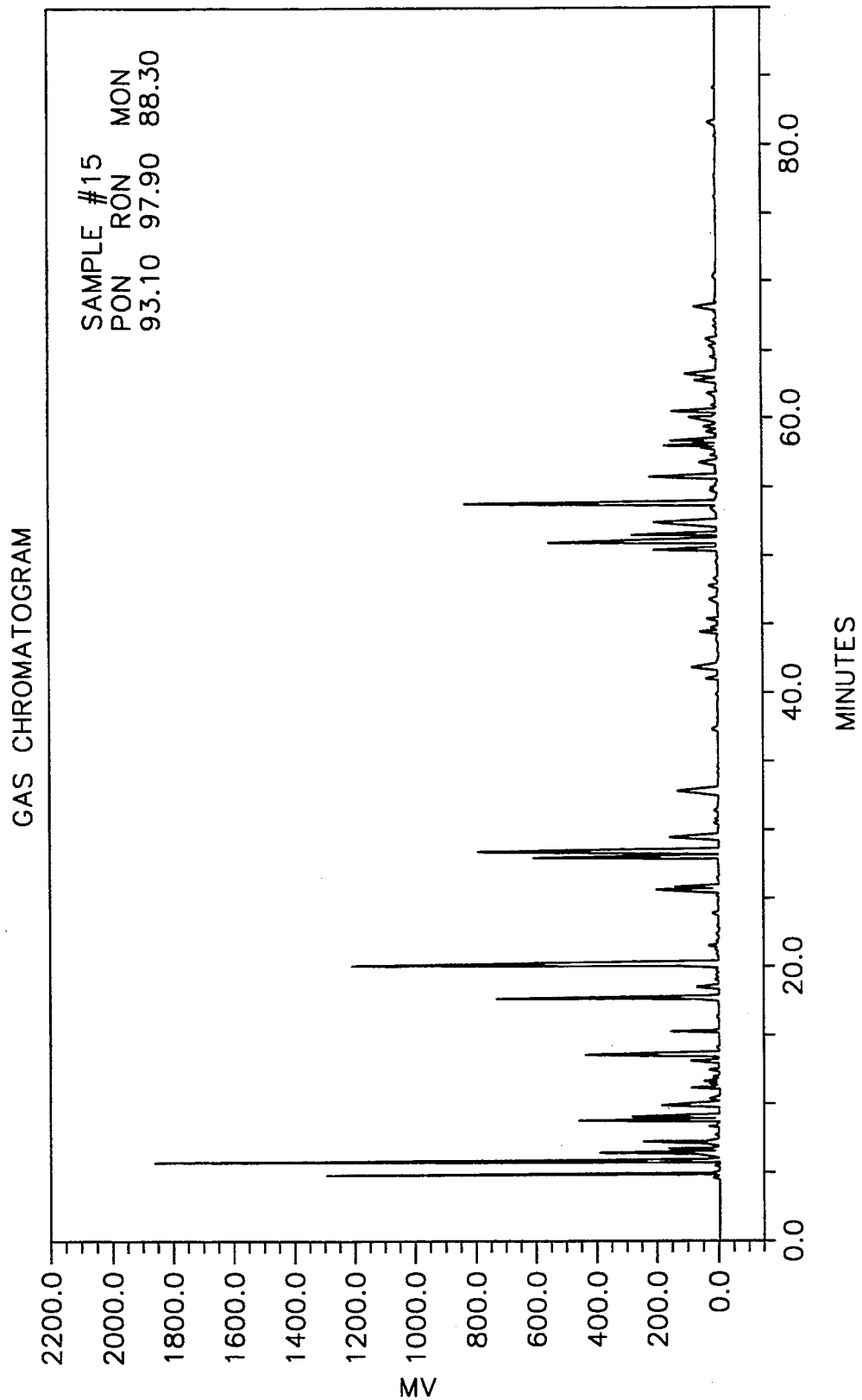

The method of the preferred embodiment, as described below, was used to generate improved estimations of octane numbers (properties of interest) of gasoline (material being analyzed). Basically, the method of the present invention concatenates data that is sensitive to trace compounds to the infrared spectral data of a calibration set of samples to create a data set that more accurately represents the total range of components contained in the samples and from which a calibration model can be developed for accurate estimation of octane numbers.

As in the prior art, the method of the present invention starts with a representative set of material (Calibration Set of Samples of gasoline). The calibration set, shown in Table 1, included samples that covered the expected range of the properties of interest. The calibration set consisted of unleaded gasolines with precisely known octane numbers. Twenty-six National Exchange Group (NEG) gasolines were selected for the calibration set because the Research (RON), Motor (MON) and Pump (PON) Octane Numbers of these samples were very accurately rated by many labs (often thirty or more) using primary reference measurement methods and then the ratings were averaged. Table 1 shows that for this NEG Calibration Set, RON ranged from 75.70 to 99.23, MON ranged from 71.60 to 88.60, and PON ranged from 73.65 to 93.92.

In near-infrared (NIR) or infrared (IR) spectroscopy, the spectra generally are presented as absorbance versus wavelength or wavenumber. Absorbance is used rather than transmittance because absorbance is proportional to the concentration of the absorbing species (Beer's Law). The absorbance A at a wavelength $\lambda$ is defined as the base-ten log of the ratio of intensity of light $I_0$ (at wavelength $\lambda$) which enters the sample to the intensity of light I (at wavelength $\lambda$) which exits the sample as shown in Equation 1:

$$A(\lambda)=\log_{10}[I_0(\lambda)/I(\lambda)]\qquad(1)$$

Equation 1 expresses the absorbance A as a continuous function of the wavelength $\lambda$. However, in practice, instruments used in NIR analysis only measure the absorbance at a fixed number of wavelengths $\lambda_1 \ldots \lambda_n$, where N is typically greater than 100 but less than 1000.

The theoretical basis for NIR analysis relies on the fundamental assumption that the spectrum of a sample contains all the information needed to predict a property of interest in the sample. That is, the property of interest (Y) is some function (F) of the spectrum. More specifically, Y is some function of the absorbances ($A_{\lambda 1}$, $A_{\lambda 2} \ldots A_{\lambda N}$) at each wavelength ($\lambda_1, \lambda_2, \ldots \lambda_N$).

Any function, regardless of complexity, can be approximated to first order, about some point $A_0 = [A_{0\lambda 1}, A_{0\lambda 2}, \ldots A_{0\lambda N}]$ in variable space, as a linear function of its variables—a Taylor series expansion about point $A_0$. That is, $$Y \approx c_0 + c_1 A_{\lambda 1} + c_2 A_{\lambda 2} + \ldots + c_N A_{\lambda N}\qquad(2)$$

Geometrically speaking, an octane-number response surface can be approximated with an equation having the form of Equation 2 which corresponds to a hyperplane that is either tangent to the surface at the point $A_0$ or that slices through the surface near point $A_0$ (as is done in chemometrics). Because an approximation worsens as the distance between points increases, it is difficult to get pure chemicals (such as iso-octane, heptane, etc.) into the same calibration equation as blended gasolines. The iso-octane and heptane points in absorbance (spectral) space are too far from the blended gasoline points for the same approximation to fit both within acceptable thresholds.

For example, the linear Taylor-series approximation to the function $Y = X^2$ about the point $X_0 = 1$ is $Y \approx -1 + 2X$. Geometrically speaking, the parabola $Y = X^2$ is approximated by the straight line $Y = -1 + 2X$ that is tangent to the parabola at $X_0 = 1$. This approximation is good for $X = 1.05$ or $X = 0.95$, but it is very poor for $X = 10$.

With chemometrics, known data points representing the curve are used instead of the functional form of the curve to find the best secant by minimizing the sums of the squares of the vertical distances from the points to the line. For example, if five X-Y pairs of data points centered around $X_0 = 1$ on the $Y = X^2$ curve (such as 0.80, 0.64; 0.90, 0.81; 1.00, 1.00; 1.10, 1.21; and 1.20, 1.44) are known, then the least squares fit to these points is the straight line given by $Y = -0.98 + 2X$. This equation for the secant line is slightly different than the equation for the tangent line described earlier (its intercept is 0.02 higher). As previously noted, this approximation is good near $X = X_0 = 1$, but poor for X far from 1, such as $X = 10$.

Most chemometric techniques such as Multiple Linear Regression (MLR), Partial Least Squares (PLS) and Principal Components Regression (PCR) result in an equation of the form shown in Equation 2, although they arrive at this type of equation by very different means, generate different regression coefficients $c_i$, and may not use all "N" of the variables. Geometrically, the resulting chemometric equation corresponds to a hyperplane that intersects the response surface in such a way as to minimize the sum of the squares of the estimation errors. The method of the preferred embodiment as explained below uses Step-Forward Multiple Linear Regression (SF-MLR) although other chemometric techniques such as PLS and PCR also can be used.

Near-infrared (NIR), mid-infrared (IR) and Raman spectra, as well as gas chromatograms of the NEG Calibration Set were obtained. The gas chromatograms provide the gasoline composition on a component by component basis. Typically there are 200 to 300 or more individual components in the gasoline. Second-derivative NIR spectra and zero-derivative IR, Raman and GC data were used. Only every tenth IR data point (a total of 460 points) and every fourth Raman data point (a total of 454 points) were used due to a computer memory limitation but all the NIR points in the range 1100-2250 nm (a total of 575 points) were used. The only two exceptions were the use of every second Raman point for Raman alone and every fifteenth IR point in NIR-IR-Raman in Table 2a.

Table 2a lists the results of the 5-parameter SF-MLR regressions performed on the NEG Calibration Set for RON, MON and PON based on NIR, IR, GC and Raman data, individually and in all possible paired and triplet combinations. The SF-MLR technique searches for the best one-parameter regression equation, then the best two-parameter equation, and so on. As the total number of parameters increases, SF-MLR may also substitute previously selected parameters with new ones to achieve a better correlation. Few substitution changes were observed in the test and none was seen which changed the order in which parameters from different techniques were selected for the NEG Calibration Set.

When analyzing the results of the different combinations of techniques as listed in Table 2a, comparisons should be made of the differences between the F-statistic and Standard Error of Calibration (SEC=Root Mean Square estimation errors) and the order in which parameters from different techniques were selected (as listed in the last row of each block of data in Table 2a) instead of the coefficient of determination (R-sq) because the sample with PON=3.65 is quite far removed from the other samples (the next lowest PON is 86.89) which makes R-sq closer to unity than it would be if the samples were evenly distributed.

For the combined NIR-GC data set it was found that the first two or three parameters selected by the SF-MLR were NIR wavelengths and the remainder were GC peaks. This implied that, after two or three NIR wavelengths, there was more information in individual GC peaks than in any individual NIR wavelengths.

The identity of the selected peaks was also informative and consistent with the notion that NIR was missing high-impact components that existed in trace amounts often less than 1%. For example, the NIR wavelengths (for MON) of 1248 nm and 1226 nm were selected first and then the GC peaks of normal heptane, normal octane and 3, 5-dimethylheptane. The concentrations of these compounds in the samples are listed in Table 1.

Like all long, straight-chain alkanes, heptane has a very low octane number (zero). Therefore, a small amount of heptane has a relatively large impact on typical gasolines whose MON values are between 80 and 90. In fact, normal heptane used alone serves as the definition of an octane number of zero. Branched octane (iso-octane) serves as the definition of an octane number of 100. Unbranched (normal) octane is a straight-chain alkane even longer than normal heptane resulting in more severe knocking and, therefore, is represented by an octane number less than zero. Normal octane was not found in an octane-number table but the next longest straight alkane (normal nonane) is rated as an octane number of $-38$. Thus, normal octane should have an octane number in the range of 0 to $-38$ and probably around $-19$.

Whenever NIR data was included, the peak first selected by the SF-MLR was an NIR peak. For combinations of NIR with IR or GC, the peak selected second was also an NIR peak. When NIR was combined with Raman, however, the second peak selected was a Raman peak. For NIR-IR-Raman and NIR-GC-Raman, the NIR and Raman peaks dominated. That is, at least 4, and sometimes all 5, of the peaks were either NIR or Raman. When the IR or GC peaks were selected, they were chosen later as the 3rd, 4th or 5th peaks.

The implication of these results is that NIR contains most of the information needed for determining octane number and collects the information relevant to octane number into a few places in the spectrum unlike mid-IR where this information is more diffused. NIR has a few voids or blind spots, however, that can be filled with GC data, Raman data, IR data or some combination of these and other data.

For the NEG Calibration Set, the best regressions for PON and RON (SEC"=0.220 and 0.211) were obtained with NIR-GC-Raman. Only for MON, did NIR-IR-Raman (SEC=0.206) do somewhat better than NIR-GC-Raman (SEC=GC-Raman were NIR-Raman and NIR-IR-Raman. However, in all cases where both NIR and Raman data were included, the NIR and Raman peaks dominated the regressions.

One Raman peak that was often selected by the SF-MLR to complement the NIR data was 1035.65 wavenumbers. To better understand the chemistry to which this Raman peak was responding, the Raman peak was regressed against the GC data and produced an R-sq=0.81 between this peak and the amount of n-$C_{11}$ (normal undecane whose blending value is below $-33$ and probably around $-53$). This is consistent with the theory that NIR is missing the trace amounts of high-impact components. The concentrations of $C_{11}$ in the set of gasolines ranged from 0.024 to 0.702 percent.

Additionally for the NEG Calibration Set, the concentration of n-$C_{11}$ was also highly correlated to the amounts of other high-impact trace components such as n-$C_{10}$, and n-$C_{12}$. The squares of the correlations between the amounts of normal $C_{11}$ in the NEG Calibration Set samples and the amounts of some other normal alkanes are:

$R^2=0.81$ for n-$C_{12}$; $R^2=0.82$ for n-$C_{10}$; $R^2=0.59$ for n-$C_9$;

$R^2=0.64$ for n-$C_7$; $R^2=0.24$ for n-$C_7$; and $R^2=0.25$ for n-$C_6$.

The intensity of Raman peaks increases with the polarizability of the sample molecule. Long-chain, normal hydrocarbons are particularly polarizable. Thus, Raman is particularly sensitive to some of the very compounds that have a high-impact on octane number but which fall into NIR's blind spots because of their low concentrations. This makes Raman data a relatively good complement to NIR data.

FIGS. 1a–d illustrate sample NIR, IR, Raman spectra and gas chromatogram, respectively, of a regular-octane gasoline (sample#1 of the NEG Calibration Set; PON=87.25). FIGS. 2a–d illustrate sample NIR, IR, Raman spectra and gas chromatogram, respectively, of an intermediate-octane gasoline (sample#13 of the NEG Calibratic,,n Set; PON=89.25). FIGS. 3a–d illustrate sample NIR, IR, Raman spectra and gas chromatogram, respectively, of a high-octane gasoline (sample#15 of the NEG Calibration Set; PON=93.10).

To determine the effect of using a "full-spectrum" analysis technique, 5-parameter SF-MLR also was performed on the principal component projections (scores) of the NIR, IR, GC and Raman data individually and in combination with the original NIR, IR, GC and Raman data. The results of these regressions are shown in Table 2b where the lower case letters denote principal component projections (scores) and upper case letters denote data from the original spectra or chromatograms.

Twenty-five principal components were calculated for the data from each technique (NIR, IR, Raman and GC) to insure that all degrees of freedom were used. SF-MLR usually selected scores corresponding to the lower numbered principal components. Overall, 42% of the scores selected corresponded to principal components 1-3, 68% to principal components 1-6 and 84% to principal components 1-9.

As before, the regressions based on combining two techniques were generally better than regressions based on a single technique. In particular, the original GC and Raman data effectively complemented the NIR and IR principal-component scores. Better 5-parameter regressions were obtained with combinations of the original data alone (Table 2a) than with combinations of the principal-component scores and the original (Table 2b).

One disadvantage of gas chromography is that it takes approximately 20 minutes to 2 hours to obtain a chromatogram which is slower than spectroscopic techniques that can generate a spectrum in about a minute. Thus, for the combined NIR-GC technique, the preferred embodiment performs NIR-GC estimations approximately every minute using the current NIR data in combination with the most recent GC data (obtained in the most recent run that occurred from about 20 minutes to 2 hours previously). If the amounts of high-impact trace components are not changing rapidly, then these periodic GC updates would be adequate to provide a good balance between rapid analysis and accuracy.

As discussed above in reference to the Maggard patent, small differences in octane-number correlation coefficients for different wavelength regions (such as those described by Maggard) often can be attributed simply to the use of different calibration sets. As an example, a diverse group of 277 samples of gasolines obtained from twenty cities around the United States was used as the second calibration set. Each of the gasolines in this 277-sample Calibration Set was rated on the engines of a single laboratory (unlike the 26 gasoline samples in the NEG Calibration Set discussed earlier that were each rated by many laboratories).

Using the same hardware (NIR Systems Model 6500) to collect the spectra and the same software and spectral processing (2nd derivatives, with segment 20 and gap 0) that Maggard used, the best PON-correlating single wavelength in the region 400–2500 nm produced by the 277-sample Calibration Set was 928 nm (R=0.9792, SEC=0.512), which is close to the 932 mm best PON-correlating single wavelength found by Kelly. Interestingly, the 277-sample Calibration Set used only a 4 mm pathlength whereas Kelly used 20 mm. This made the third overtone peaks for the 277-sample Calibration Set one-fifth the size of Kelly's. Nevertheless, the third overtone was still selected for the 277-sample Calibration Set in preference to the second overtone. Excluding the 928 nm peak, the next best peak is at 1036 nm (R=0.9654) which is still not in the 2nd-overtone region recommended by Maggard.

The 1220 nm wavelength that Maggard found to be best (R=0.9887, SEC=0.414) for his training set also was tested on the 277-sample Calibration Set. The PON-correlation to 1220 nm for the 277-sample Calibration Set was R=0.9049 with SEC=1.08, which is substantially worse than the 928 nm PON correlation (R=0.9792 with SEC=0.512) described above. The best PON-correlating individual 2nd-overtone wavelength for the 277-sample Calibration Set was 1208 nm which had R=0.9640 and SEC=0.673. This data again emphasizes that the best correlating wavelengths depend on the calibration set.

Figure 4A:
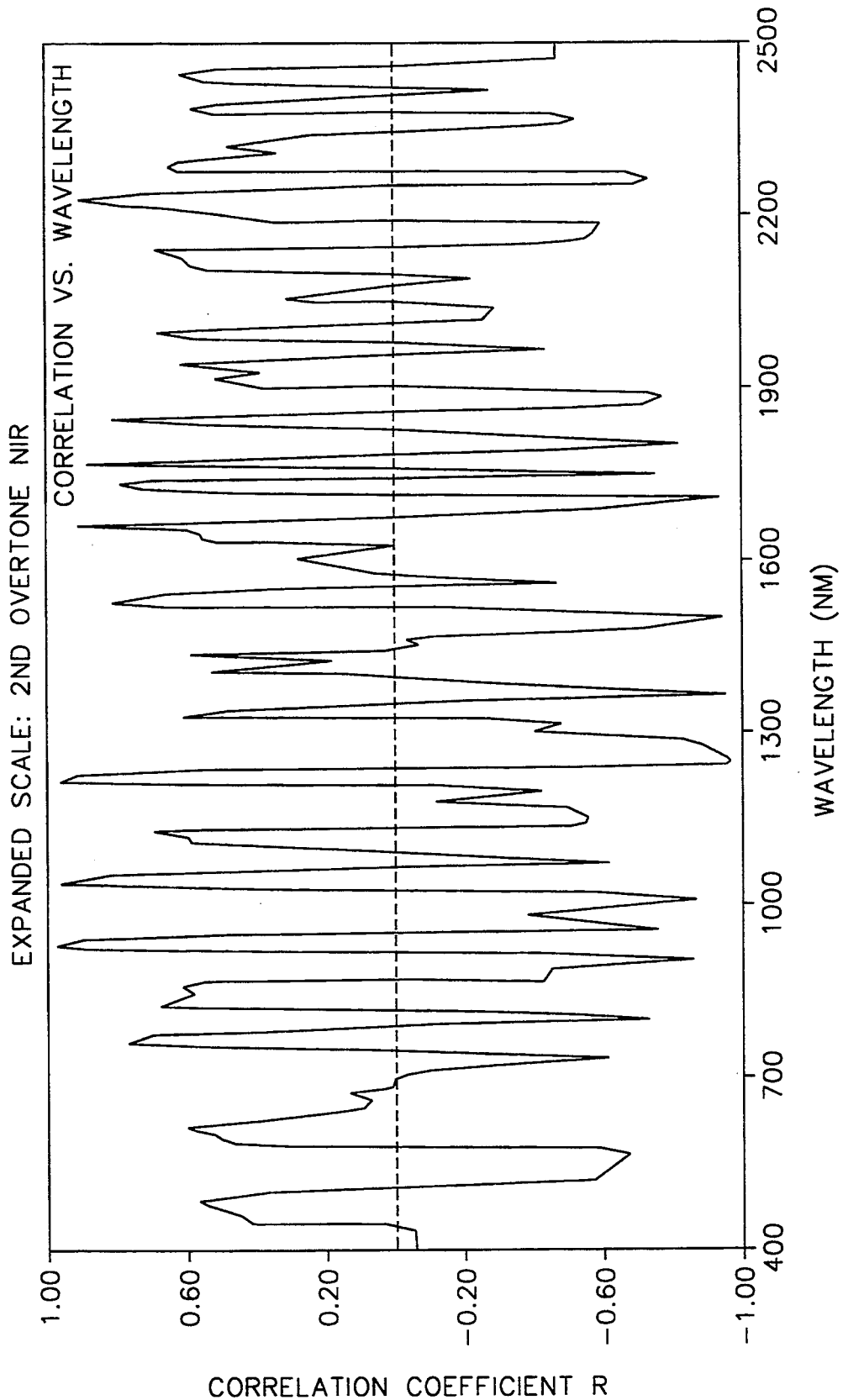
FIG. 4a is a plot of the PON correlation to single wavelengths in the visible and NIR range 400–2500 nm for the 277-sample Calibration Set.

There are many wavelengths in each of the ovennone regions of the near-infrared that are highly correlated to octane number. FIG. 4a plots the correlation coefficient versus wavelength for single-wavelength correlations to PON over the visible and entire NIR range of 400–2500 nm for the 277-sample Calibration Set. There are numerous correlation peaks (and valleys) where the wavelengths are highly correlated (or anti-correlated) to PON. The first overtones of C-H are within about 100 nm of 1700 nm, the second ovennones are within about 100 nm of the 1200 nm, and the third ovennones are within about 100 nm of 950 nm. Conceptually, each higher overtone is an ever-fainter "echo" of the corresponding mid-infrared fundamental frequency of molecular vibration.

The peaks of the best correlating wavelength regions are at 928 nm (R=0.9733), 1036 nm (R=0.9654), 1208 nm (R=0.9640), 1244 nm (R=−0.9623), 1360 run (R=−0.9473), 1486 nm (R=−0.9515) and 1694 nm (R=−0.9428). Depending on the calibration set, pathlength and instrument used, the 1st, 2nd or 3rd-overtone correlation peaks could end closer to unity (R=1.0) than the others.

To test the extent of redundancy in the data in the various overtones, intercorrelations between the wavelengths of best-correlating peaks of the 2nd-derivative spectra were calculated. The results are summarized in Table 3 and show a high degree of intercorrelation. The magnitudes of the correlation coefficients (R) between 3rd-overtone peaks (928 nm, 1036 nm) and 2nd-overtone peaks (1208 ran, 1244 nm) that correlated to PON all exceed 0.96.

Figure 4B:
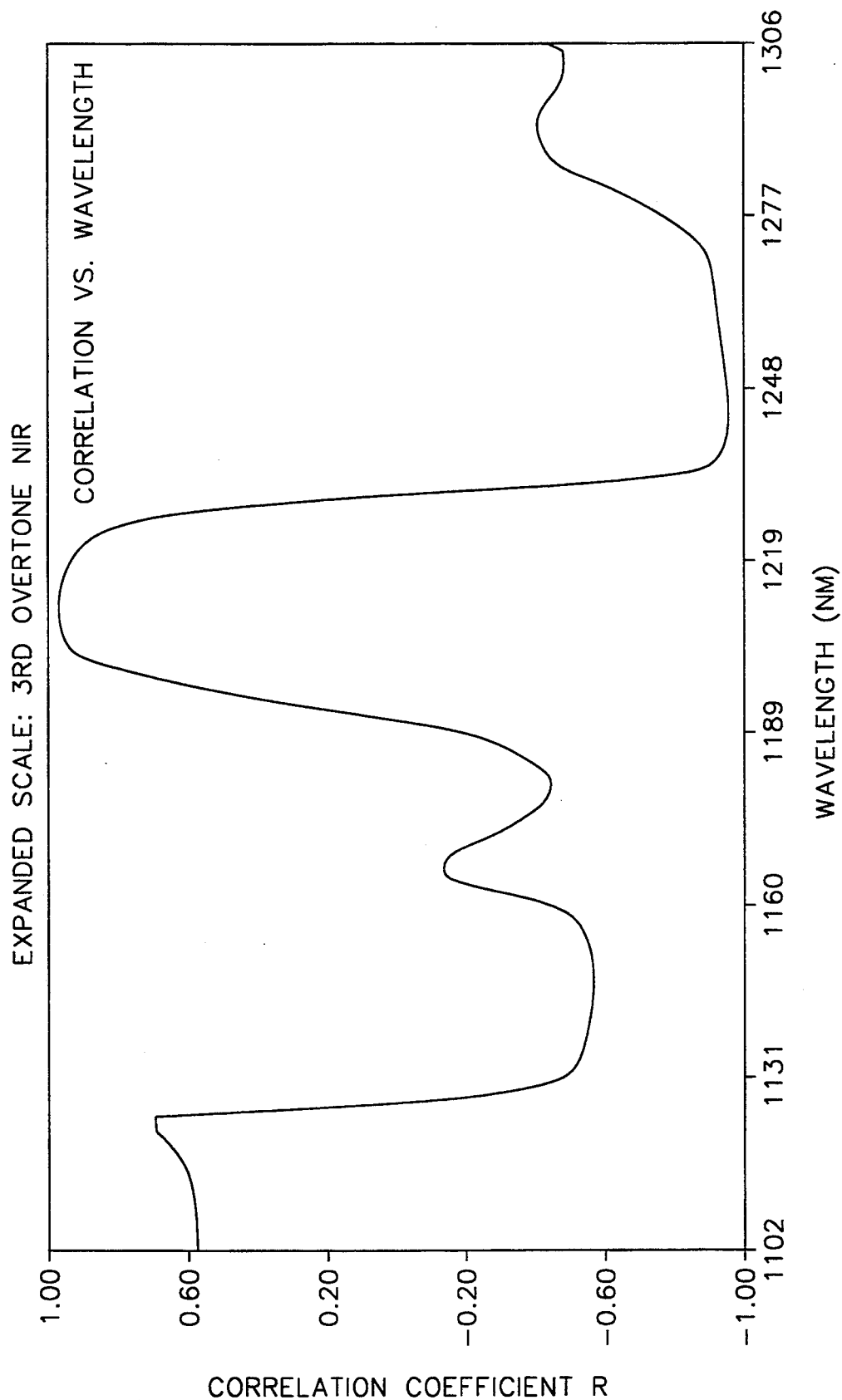
FIG. 4b is an expanded-scale plot of PON correlation for 3rd overtone of NIR.
Figure 4C:
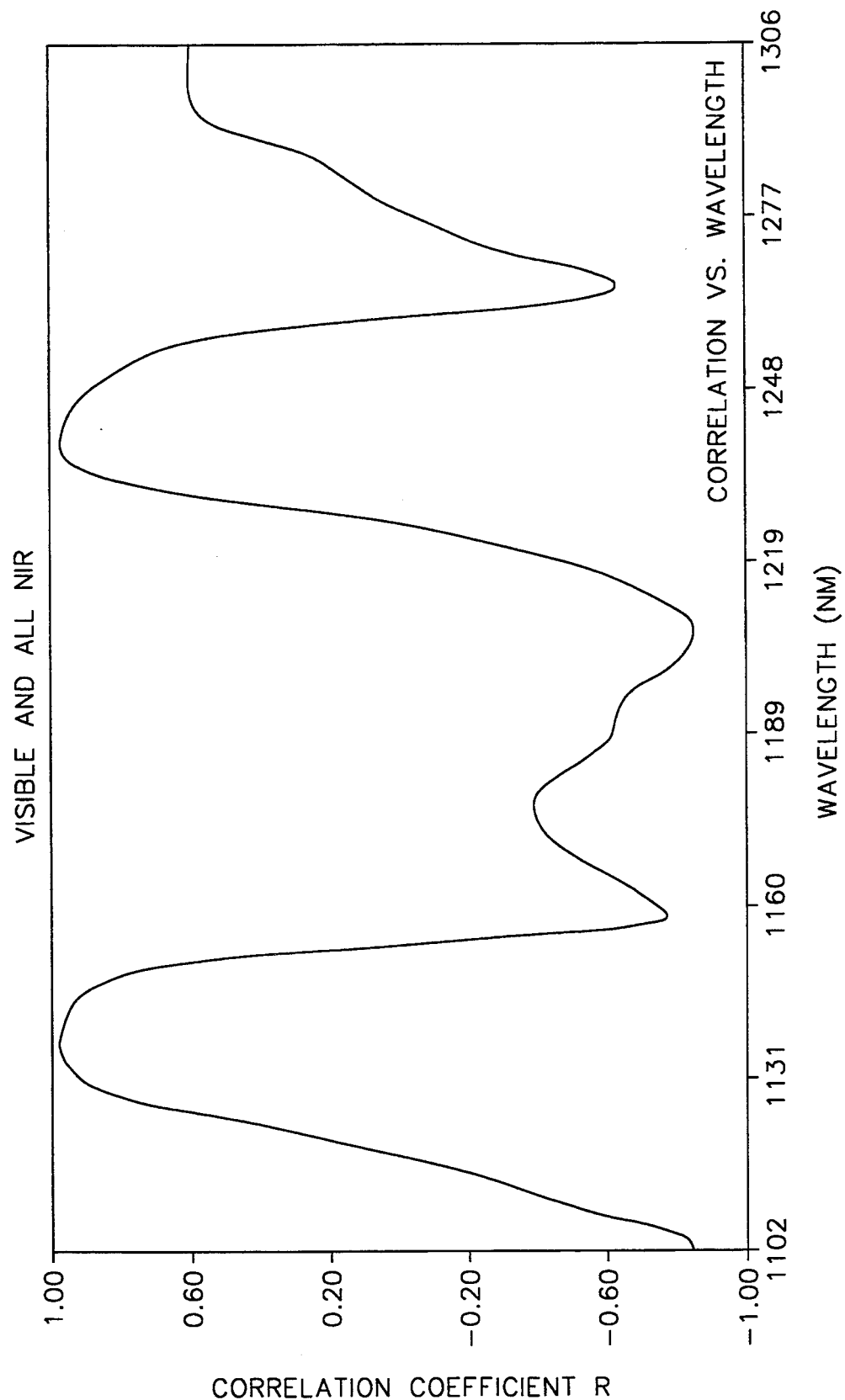
FIG. 4c is an expanded scale plot of PON correlation for 2nd overtone of NIR.

FIGS. 4b and 4c show an expanded-scale of the 892–1106 nm and 1102–1306 nm regions of FIG. 4a. FIG. 4c is analogous to Maggard's FIG. 2 in U.S. Pat. No. 4,963,745. Good PON-correlation over the 1189–1230 nm region was found but the correlation is better towards the shorter wavelength side of this region (a slightly negative-sloping plateau) while Maggard's is better towards the longer wavelength side (a slightly positive-sloping plateau). FIG. 4b shows that for the 277-sample Calibration Set, better PON correlations are obtained for both 928 nm and 1036 nm than for any wavelength in the range deemed preferable by Maggard ( 1196–1230 nm).

A recent U.S. Pat. No. (5,139,334) issued to Clarke in 1992 discusses the use of Raman data on a stand-alone basis. Clarke teaches that the octane numbers of gasolines can be correlated to Raman spectral areas integrated over two or more wavenumber regions and, in particular, to the ratio of the areas under the 1006 and 1450 wavenumber peaks or to the ratio of the integrated spectrum below 2000 wavenumbers to that above 2000 wavenumbers. Using the method of the preferred embodiment, an attempt was made to correlate both the ratio 1006/1450 and the ratio 2000+/2000- to the octane numbers of the gasolines in the 26-sample NEG Calibration Set. Very poor correlations ($R^2$ less than 0.10) were obtained possibly due to Clarke's correlation being too specific to his 11-sample training set and/or the NEG Calibration Set being more diverse than Clarke's.

For the NEG Calibration Set of gasolines used with the method of the preferred embodiment, good correlations to octane number were obtained with Raman spectra alone but at wavenumbers other than those suggested by Clarke. For all three types of octane number (RON, MON, PON), 2847.63 cm$^{-1}$ was the most important wavenumber (with $R^2=0.9359$ for PON and $R^2=0.8851$ for RON and $R^2=0.9641$ for MON). The next wavenumber selected was 810.92 cm$^{-1}$ for PON (cumulative $R^2=0.9727$), 2693.33 cm$^{-1}$ for RON (cumulative $R^2=0.9552$), and 1034.65 cm$^{-1}$ for MON (cumulative $R^2=0.9786$).

Although single techniques such as NIR or Raman alone can produce good results for specific sample sets, better estimations of octane numbers for the full range of samples were obtained when NIR spectra were supplemented with data from other techniques such as Raman.

While the foregoing has described the preferred embodiment of the present invention, it is to be understood that various changes may be made without departing from the scope of the invention as set forth in the appended claims.

The following is a glossary of parameters and terms used in the specification:

$\lambda_i$ = i-th wavelength
$A_{\lambda i}$ = absorbance at i-th wavelength
N = number of wavelengths
$c_0$ = offset constant
$c_i$ = regression coefficient for absorbance $A_{\lambda i}$ at wavelength $\lambda_i$
I = intensity of light
R = coefficient of correlation
R-sq or $R^2$ = coefficient of determination
RON and MON = research and motor octane number, respectively
PON = pump (or "road") octane number = (RON+MON)/2 = (R+M)/2
SEC = standard error of calibration
Trace Compound = compound existing in low concentrations (on the order of 1%)
Augmented Spectrum = NIR and/or IR spectrum augmented by portions of a Raman spectrum and/or gas chromatogram of the same sample
Primary Reference Method = a generally accepted direct laboratory analysis technique for determining a chemical or physical property of a sample; used as the "actual" value of a property when developing a correlation between that property of a sample and the sample's infrared spectrum Calibration Set=representative samples for which spectra are obtained and for which properties of interest are measured by a primary reference method (also called the training set of samples)

TABLE 1

OCTANE RATINGS OF CALIBRATION SET AND % OF SOME HIGH-IMPACT TRACE COMPONENTS

| | OCTANE RATINGS | | | WEIGHT PERCENTAGES | | | |
|---|---|---|---|---|---|---|---|
| | PON | RON | MON | NORMAL HEPTANE | NORMAL OCTANE | 3,5-DIMETHYL HEPTANE | n-$C_{11}$ |
| 01 | 87.25 | 91.90 | 82.60 | 3.321 | 0.530 | 0.160 | 0.065 |
| 02 | 92.16 | 96.18 | 88.15 | 0.820 | 0.384 | 0.187 | 0.046 |
| 03 | 92.57 | 97.49 | 87.65 | 1.586 | 0.451 | 0.111 | 0.024 |
| 04 | 88.84 | 93.48 | 84.21 | 0.934 | 0.404 | 0.157 | 0.123 |
| 05 | 89.09 | 93.62 | 84.57 | 2.338 | 0.728 | 0.180 | 0.027 |
| 06 | 89.89 | 94.91 | 84.88 | 1.373 | 0.889 | 0.257 | 0.128 |
| 07 | 91.84 | 96.05 | 87.63 | 1.473 | 0.504 | 0.162 | 0.028 |
| 08 | 86.96 | 91.20 | 82.72 | 1.188 | 0.662 | 0.188 | 0.069 |
| 09 | 91.20 | 96.01 | 86.39 | 1.087 | 0.296 | 0.091 | 0.032 |
| 10 | 88.30 | 92.91 | 83.69 | 1.019 | 0.411 | 0.141 | 0.066 |
| 11 | 92.45 | 98.10 | 86.80 | 0.131 | 0.323 | 0.045 | 0.099 |
| 12 | 73.65 | 75.70 | 71.60 | 3.428 | 1.422 | 0.075 | 0.702 |
| 13 | 89.25 | 94.00 | 84.50 | 0.742 | 0.471 | 0.061 | 0.106 |
| 14 | 90.20 | 95.70 | 84.70 | 0.799 | 0.525 | 0.069 | 0.116 |
| 15 | 93.10 | 97.90 | 88.30 | 0.297 | 0.116 | 0.140 | 0.034 |
| 16 | 93.92 | 99.23 | 88.60 | 0.903 | 0.308 | 0.143 | 0.024 |
| 17 | 87.10 | 92.80 | 81.40 | 1.061 | 0.690 | 0.087 | 0.161 |
| 18 | 92.11 | 97.48 | 86.74 | 0.808 | 0.366 | 0.060 | 0.058 |
| 19 | 89.25 | 93.99 | 84.51 | 0.765 | 0.465 | 0.059 | 0.096 |
| 20 | 91.15 | 96.00 | 86.30 | 0.320 | 0.384 | 0.078 | 0.044 |
| 21 | 87.48 | 91.94 | 83.03 | 0.254 | 0.422 | 0.050 | 0.112 |
| 22 | 89.00 | 93.70 | 84.30 | 0.305 | 0.475 | 0.063 | 0.101 |
| 23 | 92.85 | 98.20 | 87.50 | 0.351 | 0.342 | 0.048 | 0.019 |
| 24 | 86.89 | 91.88 | 81.90 | 0.418 | 0.614 | 0.084 | 0.057 |
| 25 | 88.00 | 92.80 | 83.20 | 0.252 | 0.622 | 0.084 | 0.037 |
| 26 | 87.14 | 92.71 | 81.56 | 0.629 | 0.640 | 0.081 | 0.156 |

TABLE 2a

SUMMARY OF ESTIMATION OF PON, MON AND RON NEG VALUES FROM DIFFERENT SPECTRA

| | N | I | G | R | NI | NG | NR |
|---|---|---|---|---|---|---|---|
| | | | PON | | | | |
| R-sq | 0.991 | 0.973 | 0.974 | 0.995 | 0.991 | 0.993 | 0.996 |
| R-sq (adj) | 0.989 | 0.967 | 0.967 | 0.994 | 0.989 | 0.991 | 0.995 |
| F | 461.3 | 146.1 | 149.1 | 842.2 | 461.3 | 572.4 | 981.6 |
| SEC | 0.402 | 0.708 | 0.701 | 0.298 | 0.402 | 0.361 | 0.276 |
| Min. Res. | −0.79 | −1.24 | −0.99 | −0.53 | −0.79 | −1.08 | −0.49 |
| Max. Res. | 0.85 | 0.89 | 1.35 | 0.40 | 0.85 | 0.50 | 0.43 |
| Std. Error | 0.071 | 0.124 | 0.122 | 0.052 | 0.070 | 0.063 | 0.048 |
| Peaks | NNNNN | IIIII | GGGGG | RRRRR | NNNNN | NNNGG | NRNNR |
| | | | RON | | | | |
| R-sq | 0.986 | 0.993 | 0.974 | 0.995 | 0.988 | 0.991 | 0.998 |
| R-sq (adj) | 0.982 | 0.991 | 0.968 | 0.994 | 0.987 | 0.989 | 0.997 |
| F | 277.1 | 526.4 | 151.4 | 805.2 | 342.3 | 450.1 | 11866 |
| SEC | 0.587 | 0.427 | 0.789 | 0.346 | 0.529 | 0.462 | 0.228 |
| Min. Res. | −1.53 | −0.69 | −1.16 | −0.56 | −0.93 | −0.78 | −0.48 |
| Max. Res. | 1.16 | 0.73 | 1.16 | 0.48 | 0.63 | 0.75 | 0.33 |
| Std. Error | 0.102 | 0.075 | 0.135 | 0.061 | 0.093 | 0.081 | 0.040 |
| Peaks | NNNNN | IIIII | GGGGG | RRRRR | NNINN | NNGNN | NRRNR |
| | | | MON | | | | |
| R-sq | 0.990 | 0.956 | 0.984 | 0.994 | 0.989 | 0.997 | 0.997 |
| R-sq (adj) | 0.987 | 0.945 | 0.979 | 0.993 | 0.986 | 0.996 | 0.996 |
| F | 389.2 | 87.7 | 238.0 | 684.7 | 364.4 | 1188 | 1157.3 |
| SEC | 0.386 | 0.800 | 0.492 | 0.292 | 0.399 | 0.222 | 0.225 |
| Min. Res. | −0.75 | −1.28 | −0.82 | −0.54 | −0.75 | −0.32 | −0.45 |
| Max. Res. | 0.41 | 1.68 | 0.986 | 0.64 | 0.61 | 0.46 | 0.44 |
| Std. Error | 0.068 | 0.140 | 0.086 | 0.051 | 0.070 | 0.039 | 0.039 |
| Peaks | NNNNN | IIIII | GGGGG | RRRRR | NNINI | NNGGG | NRNNR |

| | IG | IR | GR | NIG | NIR | NGR | IGR |
|---|---|---|---|---|---|---|---|
| | | | PON | | | | |
| R-sq | 0.978 | 0.989 | 0.991 | 0.993 | 0.996 | 0.997 | 0.991 |
| R-sq (adj) | 0.973 | 0.986 | 0.989 | 0.991 | 0.995 | 0.997 | 0.989 |
| F | 179.3 | 345.9 | 444.0 | 572.4 | 981.6 | 1553.1 | 444.0 |
| SEC | 0.640 | 0.464 | 0.410 | 0.361 | 0.276 | 0.220 | 0.410 |
| Min. Res. | −1.07 | −0.80 | −0.77 | −1.08 | −0.49 | −0.46 | −0.77 |
| Max. Res. | 1.06 | 1.02 | 0.99 | 0.50 | 0.43 | 0.34 | 0.99 |

TABLE 2a-continued

SUMMARY OF ESTIMATION OF PON, MON AND RON NEG VALUES FROM DIFFERENT SPECTRA

| | | | | | | | |
|---|---|---|---|---|---|---|---|
| Std. Error | 0.112 | 0.081 | 0.072 | 0.063 | 0.048 | 0.039 | 0.072 |
| Peaks | GGIGI | RRRIR | RGRRG | NNNGG | NRNNR | NRGNN | RGRRG |
| | | | RON | | | | |
| R-sq | 0.974 | 0.994 | 0.979 | 0.991 | 0.998 | 0.998 | 0.986 |
| R-sq (adj) | 0.968 | 0.992 | 0.975 | 0.989 | 0.998 | 0.998 | 0.983 |
| F | 151.4 | 613.8 | 240.9 | 450.1 | 2030.8 | 2175.4 | 389.9 |
| SEC | 0.789 | 0.396 | 0.701 | 0.462 | 0.218 | 0.211 | 0.574 |
| Min. Res. | −1.16 | −1.02 | −1.30 | −0.78 | −0.46 | −0.48 | −0.93 |
| Max. Res. | 1.16 | 0.76 | 1.12 | 0.75 | 0.29 | 0.40 | 1.14 |
| Std. Error | 0.138 | 0.069 | 0.126 | 0.081 | 0.038 | 0.037 | 0.100 |
| Peaks | GGGGG | RRRRR | RGRGR | NNGNN | NRRNI | NRRNG | RGRIR |
| | | | MON | | | | |
| R-sq | 0.990 | 0.989 | 0.992 | 0.997 | 0.997 | 0.997 | 0.994 |
| R-sq (adj) | 0.988 | 0.986 | 0.990 | 0.996 | 0.996 | 0.996 | 0.993 |
| F | 411.1 | 348.7 | 607.4 | 1188.0 | 1381.5 | 1157.3 | 720.2 |
| SEC | 0.376 | 0.408 | 0.339 | 0.222 | 0.206 | 0.225 | 0.285 |
| Min. Res. | −0.74 | −0.55 | −0.50 | −0.32 | −0.38 | −0.45 | −0.71 |
| Max. Res. | 0.49 | 0.74 | 0.63 | 0.46 | 0.28 | 0.44 | 0.49 |
| Std. Error | 0.066 | 0.072 | 0.059 | 0.039 | 0.036 | 0.039 | 0.050 |
| Peaks | GGIGG | RRRRI | RGGGG | NNGGG | NRNIR | NRNNR | RGGIR |

N = NIR;
I = IR;
G = GC;
R = Raman;
SEC = Root MSE
Min., Max., and Std. Error refer to residuals TABLE 2b

SUMMARY OF ESTIMATION OF PON, MON AND RON NEG VALUES FROM DIFFERENT SPECTRA

| | n | i | g | r | nI | nG | nR | iN | iG |
|---|---|---|---|---|---|---|---|---|---|
| | | | | PON | | | | | |
| R-sq | 0.966 | 0.848 | 0.944 | 0.950 | 0.969 | 0.993 | 0.986 | 0.991 | 0.981 |
| R-sq (adj) | 0.958 | 0.809 | 0.931 | 0.937 | 0.962 | 0.991 | 0.983 | 0.989 | 0.977 |
| F | 114.4 | 22.2 | 68.0 | 75.9 | 125.8 | 527.0 | 282.1 | 461.3 | 210.6 |
| SEC | 0.797 | 1.69 | 1.02 | 0.97 | 0.761 | 0.376 | 0.513 | 0.402 | 0.592 |
| Min. Res. | −1.17 | −3.69 | −2.13 | −2.42 | −1.42 | −0.61 | −0.97 | −0.79 | −0.99 |
| Max. Res. | 1.66 | 1.69 | 1.82 | 1.72 | 1.31 | 0.58 | 0.97 | 0.85 | 1.20 |
| Std. Error | 0.1 | 0.3 | 0.2 | 0.2 | 0.1 | 0.1 | 0.1 | 0.1 | 0.1 |
| Peaks | nnnnn | iiiii | ggggg | rrrrr | InInI | GGnGG | RnnRR | NNNNN | GGiGG |
| | | | | RON | | | | | |
| R-sq | 0.966 | 0.874 | 0.936 | 0.944 | 0.97 | 0.98 | 0.994 | 0.988 | 0.9725 |
| R-sq (adj) | 0.958 | 0.843 | 0.919 | 0.93 | 0.962 | 0.975 | 0.992 | 0.985 | 0.966 |
| F | 114.8 | 27.8 | 58 | 67.4 | 128.3 | 199.6 | 613.8 | 336.1 | 141.5 |
| SEC | 0.903 | 1.74 | 1.25 | 1.16 | 0.855 | 0.689 | 0.396 | 0.533 | 0.816 |
| Min. Res. | −1.25 | −3.01 | −2.59 | −2.65 | −1.8 | −1.4 | −1.02 | −0.91 | −1.54 |
| Max. Res. | 1.92 | 4.23 | 2.51 | 2.18 | 1.29 | 0.83 | 0.76 | 1 | 1.88 |
| Std. Error | 0.16 | 0.31 | 0.22 | 0.2 | 0.15 | 0.12 | 0.07 | 0.09 | 0.15 |
| Peaks | nnnnn | iiiii | ggggg | rrrrr | InInI | GGnGG | RRRRR | NNiii | GGGii |
| | | | | MON | | | | | |
| R-sq | 0.964 | 0.861 | 0.958 | 0.947 | 0.963 | 0.987 | 0.986 | 0.988 | 0.977 |
| R-sq (adj) | 0.956 | 0.826 | 0.947 | 0.934 | 0.954 | 0.984 | 0.982 | 0.985 | 0.971 |
| F | 108.4 | 24.8 | 90 | 71.5 | 105.4 | 307.1 | 280.1 | 332.5 | 166.8 |
| SEC | 0.723 | 1.43 | 0.79 | 0.881 | 0.732 | 0.434 | 0.454 | 0.418 | 0.586 |
| Min. Res. | −1.1 | −3.08 | −1.33 | −2.19 | −1.78 | −0.69 | −0.84 | −0.68 | −0.8 |
| Max. Res. | 1.4 | 2.26 | 2.06 | 1.32 | 1.17 | 0.76 | 0.56 | 0.8 | 1.48 |
| Std. Error | 0.13 | 0.25 | 0.14 | 0.15 | 0.13 | 0.08 | 0.08 | 0.07 | 0.1 |
| Peaks | nnnnn | iiiii | ggggg | rrrrr | IIInn | GGnGG | RRRRR | NNNiI | GGGiG |

| | iR | gN | gI | gR | rN | rI | rG |
|---|---|---|---|---|---|---|---|
| | | | PON | | | | |
| R-sq | 0.984 | 0.994 | 0.966 | 0.987 | 0.993 | 0.978 | 0.978 |
| R-sq (adj) | 0.980 | 0.992 | 0.958 | 0.984 | 0.992 | 0.972 | 0.972 |
| F | 240.9 | 623.7 | 114.0 | 310.0 | 582.5 | 175.8 | 173.6 |
| SEC | 0.554 | 0.346 | 0.798 | 0.489 | 0.358 | 0.645 | 0.651 |
| Min. Res. | −1.17 | −0.65 | −1.41 | −1.10 | −0.61 | −1.23 | −1.34 |
| Max. Res. | 1.23 | 0.60 | 0.89 | 0.96 | 0.49 | 1.09 | 0.99 |
| Std. Error | 0.1 | 0.1 | 0.1 | 0.1 | 0.1 | 0.1 | 0.1 |
| Peaks | RRRRR | NNgNN | IIIIgI | RRRgR | NNNNr | rrIrr | GGrGG |
| | | | RON | | | | |
| R-sq | 0.93 | 0.991 | 0.993 | 0.93 | 0.99 | 0.973 | 0.974 |
| R-sq (adj) | 0.912 | 0.989 | 0.991 | 0.912 | 0.988 | 0.967 | 0.968 |
| F | 52.7 | 438.5 | 526.4 | 52.7 | 406.1 | 146.2 | 151.5 |
| SEC | 1.31 | 0.468 | 0.427 | 1.31 | 0.486 | 0.803 | 0.789 |
| Min. Res. | −1.79 | −1.07 | −0.69 | −1.79 | −0.81 | −1.62 | −1.16 |
| Max. Res. | 2.19 | 0.6 | 0.73 | 2.19 | 0.96 | 1.2 | 1.16 |

TABLE 2b-continued

SUMMARY OF ESTIMATION OF PON, MON AND RON NEG VALUES
FROM DIFFERENT SPECTRA

|  | | | | | | | |
|---|---|---|---|---|---|---|---|
| Std. Error | 0.23 | 0.08 | 0.07 | 0.23 | 0.09 | 0.14 | 0.14 |
| Peaks | RRRRR | NNNNg | IIIII | RRRRR | NNrNN | rIIII | GGGGG |
| MON | | | | | | | |
| R-sq | 0.986 | 0.996 | 0.968 | 0.991 | 0.996 | 0.989 | 0.974 |
| R-sq (adj) | 0.982 | 0.995 | 0.957 | 0.988 | 0.994 | 0.986 | 0.967 |
| F | 280.1 | 901.1 | 112.6 | 428.5 | 875.4 | 355.6 | 149 |
| SEC | 0.454 | 0.255 | 0.709 | 0.368 | 0.258 | 0.404 | 0.619 |
| Min. Res. | −0.84 | −0.56 | −1.44 | −0.62 | −0.47 | −0.5 | −1.07 |
| Max. Res. | 0.56 | 0.44 | 1.55 | 0.54 | 0.63 | 0.79 | 0.77 |
| Std. Error | 0.08 | 0.04 | 0.12 | 0.06 | 0.05 | 0.07 | 0.11 |
| Peaks | RRRRR | NNgNg | ggIIg | RRgRg | NNrNr | IrIII | GGGrG |

PC = Principal Component;
n = NIR-PC;
i = IR-PC;
g = GC-PC;
r = Raman-PC
N = NIR;
I = IR;
G = GC;
R = Raman;
SEC = Root MSE;
Min., Max., and Std. Err. refer to residuals

TABLE 3

INTERCORRELATIONS BETWEEN ABSORBANCE DATA
AT SOME WAVELENGTHS HIGHLY CORRELATED TO PON
FOR A 277-SAMPLE SET OF U.S. GASOLINES

| nm | 928 | 1036 | 1208 | 1244 | 1360 | 1486 | 1694 | PON |
|---|---|---|---|---|---|---|---|---|
| 982 | 1.00 | .982 | .974 | −.961 | −.949 | −.943 | −.940 | .973 |
| 1036 | | 1.00 | .990 | −.975 | −.961 | −.948 | −.961 | .965 |
| 1208 | | | 1.00 | −.978 | −.983 | −.948 | −.965 | .964 |
| 1244 | | | | 1.00 | .964 | .958 | .967 | −.962 |
| 1360 | | | | | 1.00 | .942 | .972 | −.947 |
| 1486 | | | | | | 1.00 | .944 | −.952 |
| 1694 | | | | | | | 1.00 | −.943 |

We claim:

1. A method for improving the estimation of a property of interest in a random sample of a material, comprising the steps of:
   a) quantifying the property of interest for a calibration set of samples of the material using a primary reference method to form a primary reference database;
   b) generating infrared spectra for the calibration set of samples to form a calibration set of spectra;
   c) obtaining data sensitive to trace compounds in the calibration set of samples;
   d) concatenating the trace-compound-sensitive data from step c to the calibration set of spectra from step b to produce an augmented calibration set of spectra;
   e) correlating the augmented calibration set of spectra from step d with the primary reference database from step a;
   f) producing an infrared spectrum for the random sample;
   g) obtaining data sensitive to trace compounds in the random sample;
   h) concatenating the trace-compound-sensitive data from step g to the infrared spectrum from step f to produce an augmented spectrum for the random sample; and
   i) estimating the property of interest in the random sample by applying the correlation from step e to the augmented spectrum for the random sample from step h.

2. The method of claim 1 wherein the infrared spectra for steps b and f are produced by near-infrared spectroscopy.

3. The method of claim 2 wherein the trace-compound-sensitive data in steps c and g is determined by Raman spectroscopy.

4. The method of claim 2 wherein the trace-compound-sensitive data in steps c and g are determined by gas chromatography.

5. The method of claim 2 wherein the trace-compound-sensitive data in steps c and g are determined by mid-infrared spectroscopy.

6. The method of claim 2 wherein the trace-compound-sensitive data in steps c and g are determined by a combination of Raman spectroscopy and gas chromatography.

7. The method of claim 2 wherein the trace-compound-sensitive data in steps c and g are determined by a combination of Raman spectroscopy and mid-infrared spectroscopy.

8. The method of claim 2 wherein the trace-compound-sensitive data in steps c and g are determined by a combination of gas chromatography and mid-infrared spectroscopy.

9. The method of claim 2 wherein the trace-compound-sensitive data in steps c and g are determined by a combination of Raman spectroscopy, gas chromatography, and mid-infrared spectroscopy.

10. The method of claim 1 wherein the correlation step is performed with a multiple linear regression technique.

11. The method of claim 1 wherein the correlation step is performed with a step-forward multiple linear regression technique.

12. The method of claim 1 wherein the correlation step is pertained with a partial least squares technique.

13. The method of claim 1 wherein the correlation step is performed with a principal components regression technique.

14. A method for improving the estimation of octane number of a random sample of gasoline, comprising the steps of:
   a) quantifying the octane number for a calibration set of samples of gasoline using a primary reference method to form a primary reference database;
   b) generating near-infrared spectra for the calibration set of samples to form a calibration set of spectra;
   c) obtaining data sensitive to trace compounds in the calibration set of samples using Raman spectroscopy, gas chromatography, and mid-infrared spectroscopy;
   d) concatenating the trace-compound-sensitive data from step c to the calibration set of spectra from step b to produce an augmented calibration set of spectra;
   e) correlating the augmented calibration set of spectra from step d with the primary reference database from step a using a regression technique;
   f) producing a near-infrared spectrum for the random sample of gasoline;
   g) obtaining data sensitive to trace compounds in the random sample using Raman spectroscopy, gas chromatography, and mid-infrared spectroscopy;
   h) concatenating the trace-compound-sensitive data from step g to the rear-infrared spectrum from step f to produce an augmented spectrum for the random sample; and
   i) estimating the property. of interest in the random sample by applying the correlation from step e to the augmented spectrum for the random sample from step h.

* * * * *